(12) United States Patent
Hansen

(10) Patent No.: US 11,260,176 B2
(45) Date of Patent: Mar. 1, 2022

(54) AUTOINJECTOR HAVING NEEDLE SHIELD TRIGGERING

(71) Applicant: Novo Nordisk A/S, Bagsvaerd (DK)

(72) Inventor: Soeren Kjellerup Hansen, Fjenneslev (DK)

(73) Assignee: Novo Nordisk A/S, Bagsvaerd (DK)

( * ) Notice: Subject to any disclaimer, the term of this patent is extended or adjusted under 35 U.S.C. 154(b) by 588 days.

(21) Appl. No.: 16/067,214

(22) PCT Filed: Dec. 29, 2016

(86) PCT No.: PCT/EP2016/082896
§ 371 (c)(1),
(2) Date: Jun. 29, 2018

(87) PCT Pub. No.: WO2017/114934
PCT Pub. Date: Jul. 6, 2017

(65) Prior Publication Data
US 2019/0030248 A1    Jan. 31, 2019

(30) Foreign Application Priority Data

Dec. 30, 2015  (EP) .................................... 15203224

(51) Int. Cl.
*A61M 5/20*   (2006.01)
*A61M 5/24*   (2006.01)
(Continued)

(52) U.S. Cl.
CPC ........ *A61M 5/2033* (2013.01); *A61M 5/2046* (2013.01); *A61M 5/2422* (2013.01);
(Continued)

(58) Field of Classification Search
CPC .............. A61M 5/2033; A61M 5/2046; A61M 5/2422; A61M 5/2466; A61M 5/31505;
(Continued)

(56) References Cited

U.S. PATENT DOCUMENTS 2,752,918 A    7/1956  Uytenbogaar
5,658,259 A    8/1997  Pearson et al.
(Continued)

FOREIGN PATENT DOCUMENTS

CN    103476445 A    12/2013
CN    105025954 A    11/2015
(Continued)

*Primary Examiner* — Kevin C Sirmons
*Assistant Examiner* — Alexandra Lalonde
(74) *Attorney, Agent, or Firm* — Wesley Nicolas

(57) ABSTRACT

An autoinjector (100') for expelling a single dose of a drug from a held cartridge (600) comprising a piston (630). The autoinjector includes a needle shield (350, 380') axially movable from an initial extended position via a triggering position to a trigger release position. The needle shield (350, 380') is operatively coupled to a plunger release element (320', 1320) cooperating with a plunger (310, 400) to define a releasable retaining mechanism that retains the plunger release element (320', 1320) threadedly engaged with a base thread component (204', 1204) in a predefined relative rotational and axial position and against rotational bias provided by an actuator (330). The needle shield (350, 380') is configured for operating the retaining mechanism to release the retaining of the plunger release element (320', 1320) and the base thread component (204', 1204) from the predefined relative rotational and axial position upon the needle shield (350, 380') being moved into the trigger release position.

16 Claims, 16 Drawing Sheets

Figure 1A:
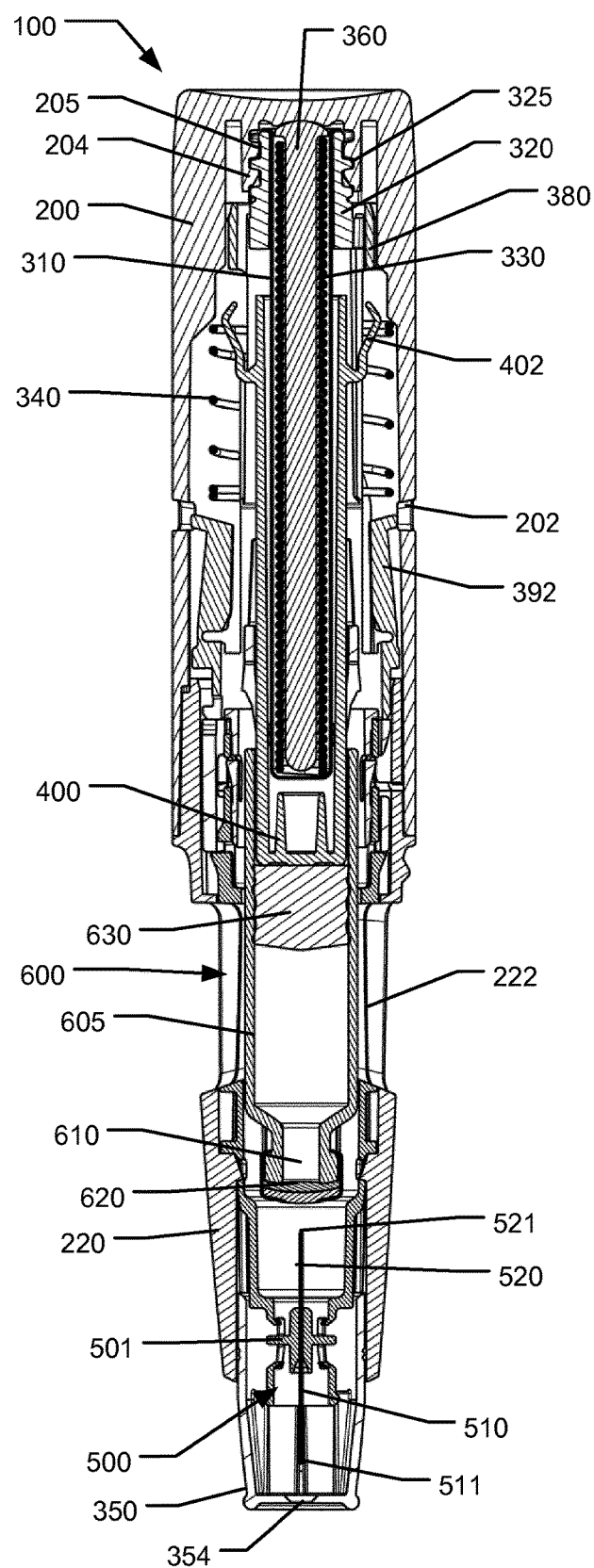

(51) Int. Cl.
*A61M 5/315* (2006.01)
*A61M 5/32* (2006.01)
*A61M 5/31* (2006.01)

(52) U.S. Cl.
CPC ...... *A61M 5/2466* (2013.01); *A61M 5/31505* (2013.01); *A61M 5/31568* (2013.01); *A61M 5/31585* (2013.01); *A61M 5/31591* (2013.01); *A61M 5/326* (2013.01); *A61M 5/3271* (2013.01); *A61M 5/3243* (2013.01); *A61M 2005/206* (2013.01); *A61M 2005/208* (2013.01); *A61M 2005/2013* (2013.01); *A61M 2005/247* (2013.01); *A61M 2005/3107* (2013.01); *A61M 2005/3125* (2013.01); *A61M 2005/3247* (2013.01); *A61M 2005/3267* (2013.01)

(58) Field of Classification Search
CPC .......... A61M 5/31568; A61M 5/31585; A61M 5/31591; A61M 5/326; A61M 5/3271; A61M 5/3243; A61M 5/3272; A61M 2005/2013; A61M 2005/2026; A61M 2005/202; A61M 2005/31508; A61M 2005/3265; A61M 2005/3267; A61M 2005/208; A61M 2005/3125; A61M 5/20; A61M 5/24; A61M 5/31501; A61M 5/31565; A61M 5/31583; A61M 5/3202; A61M 2005/247; A61M 2005/206
See application file for complete search history.

(56) References Cited

U.S. PATENT DOCUMENTS

| | | | |
|---|---|---|---|
| 6,210,369 | B1 | 4/2001 | Wilmot et al. |
| 6,743,203 | B1 | 6/2004 | Pickhard |
| 7,449,012 | B2 | 11/2008 | Young et al. |
| 7,717,877 | B2 | 5/2010 | Lavi et al. |
| 9,272,098 | B2 | 3/2016 | Hourmand et al. |
| 9,981,086 | B2 | 5/2018 | Cowe et al. |
| 10,471,210 | B2 | 11/2019 | Brereton et al. |
| 2005/0261634 | A1* | 11/2005 | Karlsson ............. A61M 5/2033 604/197 |
| 2013/0289491 | A1 | 10/2013 | Kramer et al. |

FOREIGN PATENT DOCUMENTS

| | | |
|---|---|---|
| JP | 2014502881 A | 2/2014 |
| WO | 94/07553 A1 | 4/1994 |
| WO | 2008087071 A1 | 7/2008 |
| WO | 2008/116688 A1 | 10/2008 |
| WO | 2012/022810 A2 | 2/2012 |
| WO | 2013/012745 A1 | 1/2013 |
| WO | 2015144870 A1 | 10/2015 |
| WO | 2015150578 A1 | 10/2015 |

\* cited by examiner

AUTOINJECTOR HAVING NEEDLE SHIELD TRIGGERING

CROSS-REFERENCE TO RELATED APPLICATIONS

This application is a 35 U.S.C. § 371 National Stage application of International Application PCT/EP2016/082896 (published as WO 2017/114934), filed Dec. 29, 2016, which claims priority to European Patent Application 15203224.9, filed Dec. 30, 2015, the contents thereof which are incorporated by reference in their entirety.

FIELD OF THE INVENTION

The present invention relates to injection devices for injecting a medicament. In particular the present invention relates to autoinjector devices for injecting a medicament from a held cartridge and improvements relating to the performance of such injection devices.

BACKGROUND OF THE INVENTION

In relation to some diseases patients must inject a medicament on a regular basis such as once weekly, once daily or even a plurality of times each day. In order to help patients overcome fear of needles, fully automatic injection devices have been developed with the aim of making the use of the injection device as simple as possible. Such devices are typically designed such that a user shall position the injection device onto the injection site and activate the device. Such activation causes the device to insert a needle into the skin, eject a dose of the medicament and subsequently move the needle into a shielded position.

Generally, for injection devices of the above type, main attention has been directed towards devices equipped with a glass cartridge where a needle cannula is fixedly attached to the outlet end of a cartridge. Such needle cannula is initially being covered in a sterile way by a cap member that during storage acts as a stopper for the needle cannula, and which requires removal prior to use. Typically, these devices further include a needle shield portion for shielding the needle before and/or after use. Disclosure of such devices is included in U.S. Pat. Nos. 7,449,012, 7,717,877 and WO2008/116688.

Some manufacturers prefer the type of cartridge having a pierceable septum which during storage provides a seal for the cartridge outlet and where the septum, upon use, is pierced by a needle cannula. Prior art devices using this type of cartridge are disclosed in U.S. Pat. Nos. 2,752,918, 5,658,259, 6,743,203, 6,210,369 and WO94/07553. Devices of that type hold a needle assembly and a cartridge in a separated storage configuration which upon activation of the device allows for subsequent connection to establish fluid communication between cartridge and needle assembly. In addition, automatic penetration of the needle into the skin of the user for subsequent automatic delivery of the medicament is typically incorporated.

While the above devices aim at providing a high level of automation, injection devices that provide automatic insertion of the needle into the dermis also prevent the user from controlling the insertion, which can lead to uneasiness for the user.

Injection devices that provide automatic delivery of the medicament, i.e. auto-injectors, typically use a drive spring as driving force for the injection. Before use, the drive spring will be held in a pre-tensioned position from which it is released upon activation of the device. After activation the drive spring uses the energy from the tension to drive forward the piston of a cartridge.

One problem associated with auto-injectors having needle shield operated triggering is that the release mechanism typically relies on at least one component that is exerted to excessive forces and that maintains the drive spring in a state where the plunger can be released for expelling the medicament of the cartridge. The triggering principle typically relies on at least one lock component that is deformed to unlock for releasing energy from the drive spring. Due to the excessive forces provided by the drive spring such principle often results in non-optimal performance of the needle shield movement.

For such devices, drawbacks associated with lack of synchronization between the feedback of needle movement and the action of triggering might include:
  the sterility seal of the needle may be broached even though the triggering has not been effectuated,
  it is difficult for the user to predict when the device will trigger,
  if the shield is retracted slowly this may lead to a painful needle insertion,
  the triggering may be activated before the needle shield has been fully retracted causing an injection at a shallow depth.

Having regard to the above-identified kind of prior art devices, it is an object of the present invention to provide an autoinjector having an improved needle shield triggering and which enables improved control of the device during operation. It is a further object to eliminate the potential risk that static friction between cooperating triggering components prevents an autoinjector from being triggered.

Yet additional further objects of the invention are to provide measures for obtaining devices having a superior performance and, at the same time, enabling manufacture at a reduced cost.

BRIEF DESCRIPTION OF THE INVENTION

The present invention relates to an autoinjector configured for being triggered for expelling a single dose of drug from a held cartridge, the autoinjector comprising:
  a base, a drug cartridge arranged relative to the base, the cartridge comprising:
  a) an elongated body having a distal end and a proximal end and defining a central longitudinal axis, the body having a distally arranged outlet adapted for connection to a held needle, and
  b) a piston accommodated in the body, the piston configured for being driven axially in the distal direction to expel a dose of a drug through the outlet,
  a plunger adapted upon triggering for moving in a distal direction relative to an initial axial position and transferring a force to move the piston,
  an actuator providing stored energy, the actuator configured for providing a force to act on the plunger to drive the piston distally,
  a needle shield axially movable relative to the base in a proximal direction from an initial extended position via a triggering position to a trigger release position,
  wherein a plunger release element is operatively coupled to the plunger to prevent the plunger from moving distally relative to the plunger release element, wherein the plunger release element defines a thread and the base associates with a base thread component that defines a thread adapted for engaging with the thread of the plunger release element, wherein the needle shield is operatively coupled to the plunger release element and the base thread component to define a releasable retaining mechanism configured to, in an initial state where the needle shield assumes its initial extended position, retain the plunger release element threadedly engaged with the base thread component in a predefined relative rotational and axial position where the force of the actuator provides bias for urging relative rotation between the plunger release element and the base thread component in an expelling rotational direction, wherein the needle shield is configured for operating the retaining mechanism to release the retaining of the plunger release element and the base thread component from the predefined rotational and axial position upon the needle shield being moved into its trigger release position, and wherein a first pair of cooperating means operatively couples the needle shield with the base and a second pair of cooperating means operatively couples the needle shield with the plunger release element, the first pair of cooperating means and the second pair of cooperating means being configured to induce or cause relative rotation between the plunger release element and the base thread component as the needle shield moves from the initial extended position towards the triggering position so that energy stored in the actuator changes as the needle shield moves from the initial extended position towards the triggering position.

In the present context, the term "triggering position" defines a position for the needle shield wherein a triggering movement of the needle shield has been initiated which cannot be stopped and wherein the plunger is not yet released for being forced in the distal direction by the actuator. The term "trigger release position" defines a position for the needle shield wherein the plunger is released for being forced in the distal direction by the actuator.

Due to the large surfaces of cooperating parts of the base thread component and the plunger release element, a particular smooth performance may be obtained. In accordance with the invention, the force that emanates from the actuator and that acts via the threaded connection between the base thread component and the plunger release element may be chosen in order to obtain a particular desired force-distance profile for moving the needle shield relative to the base for triggering the autoinjector. For example, a high initial force may be desirable for creating a high needle shield velocity for moving the needle shield past the triggering position and further into the trigger release position where the plunger is released for being moved distally by the actuator. This ensures that the user cannot stop the movement of the needle shield after the triggering operation has been deliberately initiated.

The second pair of cooperating means that operatively couples the needle shield with the plunger release element may be provided by an interface arranged at a radial location that is larger than the diameter of the threaded connection between the plunger release element and the base thread component. Hence, a gearing is provided for effectuating rotation for moving the needle shield from the initial extended position into the triggering position.

In addition, when triggering the device, as the user moves the needle shield in the proximal direction from the initial extended position to the triggering position, the induced rotation in a rotational direction opposite to the expelling rotational direction between the plunger release element and the base thread component helps overcoming the static friction between the threads of the plunger release element and the base thread component thereby ensuring effective triggering of the device. Hereby it is avoided that static friction and stiction between the parts potentially prevents the autoinjector from being effectively triggered.

In some embodiments, the force from the actuator transfers a force on the plunger release element in the expelling rotational direction to exert a varying reaction force on the needle shield as the needle shield moves from the initial extended position towards the triggering position.

Further beneficial embodiments are obtained by forming an injection device in accordance with the definitions listed in the appended claims.

The geometries of said tracks may comprise an inclined section configured to rotate the plunger release element relative to the base thread component against the expelling rotational direction, i.e. against the force provided by the actuator, as the needle shield moves from the extended position towards the collapsed position.

Alternatively, or in addition, the geometries of said tracks may comprise an inclined section arranged to rotate the plunger release element relative to the base thread component in the rotational direction along the expelling rotational direction.

In one embodiment of the present invention the needle shield is operatively coupled to the plunger release element to define a releasable retaining mechanism configured to, in an initial state where the needle shield assumes its initial extended position, retain the plunger release element threadedly engaged with the base thread in a predefined relative rotational and axial position where the force of the actuator provides bias for urging rotation of the plunger release element relative to the base thread in an expelling rotational direction.

In another embodiment of the present invention the needle shield is configured for operating the retaining mechanism to release the retaining of the plunger release element and the base thread component from the predefined rotational and axial position upon the needle shield being moved into its trigger release position.

In yet another embodiment of the present invention, geometries of the needle shield and the plunger release element define a pair of cooperating means that operatively couples the needle shield with the plunger release element, the pair of cooperating means being configured to induce or cause relative rotation between the plunger release element and the base thread component as the needle shield moves from the initial extended position towards the triggering position.

In certain embodiments, the pair of cooperating means are formed so that the plunger release element rotates in a direction counter to the expelling rotational direction as the needle shield moves from the initial extended position towards the triggering position. In such embodiments, the cooperating means may further be formed so that the plunger release element rotates in the expelling rotational direction as the needle shield moves from the triggering position towards the trigger release position.

Still further beneficial embodiments are defined by the subject matter disclosed below.

In the autoinjector according to the invention, the device includes a needle shield triggered expelling assembly where the actuator, such as a pre-stressed actuating spring, is actuated for releasing axial movement of the plunger by a movement of the needle shield relative to the base.

The releasable retaining mechanism may define a lock. The autoinjector may be so configured that, prior to release of the lock while operatively coupling between the base thread component and the plunger release element is maintained, the force applied by the actuator transfers into a force having a force component that acts to rotate the base thread component and the plunger release element relative to each other. Depending on the particular design of the lock of the autoinjector the said force component can be utilized for designing the required force for moving the needle shield from the initial extended position to the triggering position.

The lock may be configured to include engaging first and second components having cooperating geometries that prior to activation engage to maintain the lock and which upon activation disengage and where the disengagement does not incorporate deformation of the cooperating geometries.

The cartridge body may define a proximally facing rear surface. The distally arranged outlet of the cartridge may comprise a pierceable septum adapted to be pierced by the rear needle of a needle unit having both a front needle extending in the distal direction and a rear needle extending in the proximal direction. In alternative configurations, the cartridge body outlet portion includes an injection needle fixedly attached relative to the cartridge body.

The cartridge may be mounted slideable relative to the base. In embodiments wherein the cartridge is not initially connected to a needle, the actuator may be configured to cause the plunger to move the cartridge distally for causing the rear needle to pierce the septum of the cartridge for subsequently moving the piston of the cartridge for expelling a dose.

In other embodiments, the cartridge is mounted at a fixed axial position relative to the base. In embodiments wherein the cartridge is not initially connected to a needle, the autoinjector may be configured to allow manually connecting a needle relative to the base so as to establish fluid connection between the cartridge and the needle.

In some embodiments, the base forms a housing of the device. The autoinjector may accommodate a needle that is fixedly mounted relative to the base.

In some embodiments, the front needle is configured to be manually operable relative to the needle shield such that when the needle shield is held against an injection site, manual operation of the front needle relative to the needle shield or vice versa causes manual penetration of the front needle into the injection site and causes subsequent release of the lock.

By configuring the device so that a pushing force exerted manually on a part of the device is transferred to a manual force acting on the needle for manual penetration of the front needle into the injection site, the user gains improved control of the insertion of the injection needle. At the same time, by using this configuration the needle is hidden from the user during an administration. By providing an improved control of the needle insertion procedure a potential uneasiness for the user can be alleviated. The first part of the activation movement moves the needle forward relative to the needle shield to insert the needle in the user's skin. The second part of the movement activates the expelling assembly. In particular embodiments, this allows the user to manually insert the front tip of the needle before activating the device and an administration may be stopped in time should the user wish to abort the operation.

Relative rotational movement between the plunger release element and the base is performed around a first rotational axis. In some embodiments the first rotational axis is arranged coaxially with respect to the central longitudinal axis of the body of the cartridge. In other embodiments, the first rotational axis and the central longitudinal axis are arranged non-coaxially with respect to each other.

In the context of the present disclosure, when referring to "a base thread component", "a plunger release element defining a thread", and "a base thread component being adapted for operatively coupling with the thread of the plunger release element" this shall be so construed that when the thread of the plunger release element is operatively coupled with the base thread component the relative movement between the plunger release element and the base is provided by means of a helical guiding movement. The helical guiding movement may be provided by either a direct engagement between the plunger release element and the base or by an indirect coupling via one or more further components arranged between the base and the plunger release element. Non-limiting examples of a helical guiding movement includes a threaded coupling and a track and track follower coupling. A threaded coupling may be provided by means of co-operating screw threads having a constant lead along the first rotational axis or a variable lead along the first rotational axis. A threaded component may be provided by means of a continuous threaded section or by means of a plurality of thread segments. A track and track follower coupling may define a track having a constant pitch relative to said first rotational axis or a track having a varying pitch along the first rotational axis.

When the helical guiding movement is provided by a threaded coupling, the threaded coupling may be formed as a non-self-locking threaded coupling. The threaded coupling may in exemplary embodiments be formed so that, for the initial position of the plunger, a thread segment of one component is axially interposed between two consecutive thread segments of the other component.

The thread of the plunger release element may be provided as an outer thread extending radially outwards from the plunger release element and configured to engage an inner thread component provided by the base thread component. Alternatively, the thread of the plunger release element may be provided as an inner thread component extending radially inwards from a side surface portion of an axial bore of the plunger release element configured to engage an outer thread component provided by the base thread component.

The needle may incorporate at least one cover providing a sterility barrier for covering at last the front needle of a held needle. In applications where a rear needle is present, sterility barriers for the rear needle may be incorporated. Each of the sterility barriers may be formed as a flexible cover or sheath configured as a closed cavity for accommodating at least a part of the needle, i.e. the front needle or the rear needle. The sterility barriers may be adapted to be pierced by the tip of the needle by moving the sterility barrier and the needle relatively to each other. For the front needle, the front cover may be operated for being pierced by the front needle by moving the needle shield relative to the base. For the rear needle, the rear cover may be operated for being pierced by the rear needle by moving the cartridge relative to the rear needle.

The injection device may comprise an actuator in the form of a stored energy source coupled to the plunger and configured for driving the plunger upon release of the lock. Non-limiting examples of a stored energy source include a spring element, such as a pre-strained spring, a compressed gas etc, wherein the stored energy may be accumulated during manufacture of the autoinjector. In other forms, the energy source is configured to become charged during an initial operation of the device prior to activation of the injection mechanism. The stored energy source stores sufficient energy to operate the autoinjector for expelling the total amount of drug that is intended to be expelled from a held cartridge, and, optionally, surplus energy for driving the cartridge forward for coupling to a rear needle and/or for driving the needle shield for a needle shielding operation.

In particular forms, the actuator is provided as a helical compression spring that exerts an axial force on the plunger.

The plunger may be formed as a drive ram. The drive ram may be formed as a generally elongated cylindrical member retained at its proximal end relative to the plunger release element. Further, the plunger may include or operate through a spacing member positioned between the drive ram and the piston of the held cartridge. In some embodiments of the autoinjector the actuating spring is a helical compression spring arranged internally in a longitudinal bore of the drive ram. The drive ram may be made from a metal alloy, such as stainless steel. Alternatively, the drive ram may be made from a plastic material. In embodiments that include a drive ram, the plunger release element may be freely rotatable relative to the drive ram and/or the spacing member.

The plunger may be formed to integrally define a plunger release element thereby forming a plunger thread component that initially is in threaded engagement with the base thread component. In alternative embodiments, the plunger is coupled to a separate plunger release element formed as a generally sleeve formed threaded element. The plunger release element may define a central axial opening adapted to slidably receive the proximal end of the drive ram. The plunger may be prevented from moving distally relative to the plunger release element, at least while the thread of the plunger release element is engaged with the base thread. In certain embodiments, the plunger and the plunger release element are configured for being disengaged relative to each other upon the thread of the plunger release element having travelled a predefined axial distance in the base thread. Subsequently, the plunger is allowed to move distally relative to plunger release element. Examples of engagements that may be disengaged upon rotation include keyed engagements and threaded couplings.

In some embodiments the autoinjector may include a needle shield spring which is associated with the needle shield and the needle to urge the front needle into its shielded state or to urge the needle shield into the state where the front needle is shielded. In particular embodiments the needle shield spring is an element separate from the actuator or the actuating spring. Exemplary non-limiting embodiments of a needle shield spring include a spring element, such as a helical spring acting in compression mode and/or torsion mode, a leaf spring, a plastic spring or a plastic material spring element formed separately or integrally with other components of the autoinjector.

The needle shield may be axially movable in the proximal direction relative to the base between an extended position, through a triggering position and into a collapsed position. In some embodiments, when the needle shield has been moved away from the extended position for triggering an unused device, the needle shield may be moved back in the distal direction.

In some embodiments of the autoinjector, the lock includes a first lock element that is axially movable as the needle shield moves from the extended position towards the collapsed position. The first lock element and the plunger release element define respective cooperating lock geometries configured to, prior to activation, maintain a rotational lock between the plunger release element and the base, the cooperating lock geometries being adapted to unlock to enable rotation between the plunger release element and base upon the needle shield being moved towards the collapsed position.

The first lock element may be formed integrally with the needle shield, as part of a needle shield sub-assembly or alternatively as a component separate from the needle shield but being operated by movement of the needle shield. The first lock element may be axially movable in the proximal direction relative to the base between an extended position, through a triggering position and into a collapsed position. In some embodiments, the first lock element forms a trigger element. The first lock element may be designed to follow the needle shield when the needle shield moves in a proximal direction for triggering the device. However, in some embodiments, the first lock element does not follow the needle shield for movements of the needle shield after the device has been triggered.

In particular embodiments of the autoinjector the first lock element is prevented from rotating relative to the base. The first lock element and the plunger release element define respective cooperating lock geometries configured to, prior to activation, maintain a rotational lock between the plunger release element and the first lock element, the cooperating lock geometries being adapted to unlock to enable rotation between the plunger release element and the first lock element upon the needle shield being moved towards the collapsed position.

In alternative embodiments the first lock element is allowed to rotate relative to the base when the needle shield has been pressed into its collapsed position but is prevented from rotating relative to the base when the needle shield is in the extended position. The first lock element and the plunger release element define respective cooperating geometries configured to prevent relative rotation but allowing axial displacement.

It is to be noted that, in accordance with one embodiment, the lock needs only to remain enabled, that is to remain in locking mode, in the initial storage state, i.e. prior to activation of the expelling assembly. After activation of the expelling assembly the lock is not required to enter into locking mode again, i.e. the lock elements need not prevent relative rotation between the plunger release element and the base as the needle shield is returned to its extended position.

In some embodiments of the autoinjector the base thread component is fixedly disposed relative to the base, such as by being formed integrally with the base. When the base defines the housing or a section of the housing, the base thread component is thus axially and rotationally fixed relative to the housing.

In some embodiments, a track may be formed to extend at an angle with respect to the first rotational axis, such as less than 20 degrees, alternatively less than 15 degrees, alternatively less than 10 degrees, and still alternatively less than 5 degrees. Such slightly angled axial track would in particular applications provide only a limited rotation between the plunger release element and the base thread component during axial displacement of the needle shield from the initial extended position and into the triggering position.

In other alternative embodiments of the autoinjector, wherein the base forms part of or defines a housing of the autoinjector, the base thread component is defined by a rotatable component that is axially fixed but rotatably mounted relative to the base. The lock includes a first lock element that is axially movable as the needle shield moves from the extended position towards the collapsed position. The first lock element and the rotatable component define respective cooperating lock geometries configured to, prior to activation, maintain a rotational lock between the rotatable component and the plunger, the cooperating lock geometries being adapted to unlock to enable rotation between the rotatable component and the plunger upon the needle shield being moved towards the collapsed position.

The first lock element may be prevented from rotating relative to the base. The first lock element and the rotatable component define respective cooperating lock geometries configured to, prior to activation, maintain a rotational lock between the rotatable component and the first lock element, the cooperating lock geometries being adapted to unlock to enable rotation between the rotatable component and the first lock element upon the needle shield being moved towards the collapsed position.

In such embodiments the plunger thread component may be prevented from rotating relative to the base. In such embodiments the plunger may be mounted non-rotationally relative to the base and the plunger release element may be fixedly disposed on the plunger.

In some embodiments the first lock element defines a first lock feature and the rotatable component defines a cooperating lock feature, wherein one of the first lock feature and the cooperating lock feature defines an inclined track and wherein the other of the first lock feature and the cooperating lock feature defines a track follower. In such embodiment the inclined track may be formed as a track that extends with an angle relative to the first rotational axis. Hence, when the needle shield is moved from the extended position towards the collapsed position, the lock is released while inducing a relative rotation between the first lock element and the rotatable component. Subsequent to release of the lock, i.e. when the track follower disengages the track, rotation between the first lock element and the rotatable component enabled in accordance with the threaded engagement. Rotational movement between the rotatable component and the plunger is induced by the force exerted by the actuator due to the operative coupling of the thread components of the rotatable component and the plunger.

The axial track may be formed to extend at an angle with respect to the first rotational axis, such as less than 20 degrees, alternatively less than 15 degrees, alternatively less than 10 degrees, and still alternatively less than 5 degrees. Such slightly angled axial track would provide only a limited rotation between the plunger and the base thread component during axial displacement of the needle shield from the initial extended position and into the triggering position.

In some embodiments of the autoinjector the plunger release element is only operatively coupled with the base thread component during an initial first axial displacement of the plunger whereas, in a second axial displacement, the plunger release element is released from being operatively coupled with the base thread component, i.e. by a disengagement between the thread of the plunger release element and the thread of the base thread component, allowing the plunger release element and the plunger to subsequently continue axial displacement. Such release may occur after a rotation of the plunger release element of 90 degrees, such as 180 degrees, such as 270 degrees, such as 360 degrees, such as 1 or 2 complete revolutions.

Subsequent to axial release of the plunger, the end of stroke position of the plunger may be provided by a pre-determined axial stop position of the plunger relative to the proximally facing rear surface of the cartridge. The autoinjector may be so configured that a stop geometry of the plunger directly engages the proximally facing rear surface of the cartridge. Alternatively, one or more intermediary components may be positioned between the plunger and the proximally facing rear surface of the cartridge to provide said pre-determined predetermined axial stop position of the plunger relative to the proximally facing rear surface of the cartridge.

In some embodiments of the autoinjector the plunger release element comprises a geometry having a radial dimension, such as a diameter, that is larger than the internal diameter of a cylindrical medicament section of the cartridge. In particular for autoinjectors having an actuator that stores a large amount of energy, the large dimensions of the thread component of the plunger release element enable a robust design that offers non-problematic long-term storage, even in situations where one or both of the thread components are made from a non-metallic material and where the actuator during long-term storage is kept in a pre-tensed state.

In particular embodiments, where the housing of the autoinjector has a total length of dimension L, the base thread component may be arranged to extend from the proximal end of the housing. The base thread component may be arranged to extend from the proximal end of the housing by less than 30% of L, alternatively less than 20% of L, alternatively less than 10% of L, and still alternatively less than 5% of L.

In particular embodiments, the plunger thread component, or, as applicable, the plunger release element, may be dimensioned to extend from the proximal end of the plunger in the distal direction along the plunger by a length corresponding to less than 75% of the entire plunger length, alternatively by a length corresponding to less than 50% of the entire plunger length, alternatively by a length corresponding to less than 25% of the entire plunger length, and still alternatively by a length corresponding to less than 15% of the entire plunger length.

In some embodiments of the autoinjector the device irreplaceably accommodates a cartridge within the base and wherein the cartridge cannot be removed from the device without the use of tools.

In some embodiments of the autoinjector the force acting for causing rotation between the plunger and the base for releasing the plunger from the initial axial position is at least partly exerted by the actuator. In particular embodiments, the force acting for causing rotation between the plunger and the base for releasing the plunger from the initial axial position is exclusively exerted by the actuator.

In embodiments incorporating a cartridge and a separate needle unit, the cartridge and the needle unit may be initially held in a configuration where the cartridge and the needle unit are separated by a distance. The actuator may be capable, upon release of the lock, to cause the cartridge and the rear needle to enter into the state where the cartridge septum is pierced by the rear needle and subsequently to cause the plunger to move to dispense the medicament through the needle.

The injection device may incorporate an activator which is mechanically associated with the needle so that when the activator and the needle shield is moved relative to each other it causes the front needle and the needle shield to move relative to each other. In some embodiments the needle substantially follows movement of the activator as the activator moves relative to the needle shield. In particular embodiments, the needle is attached to the activator in a way preventing relative axial movements between the activator and the needle.

In some embodiments the activator is configured to define a housing section which at least partly accommodates the cartridge and where the housing section is adapted to be gripped by the hand of the user. In such embodiment, the activator may be coupled to the needle to transfer a force from the activator to the needle when the activator is moved relative to the needle shield.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figure 1B:
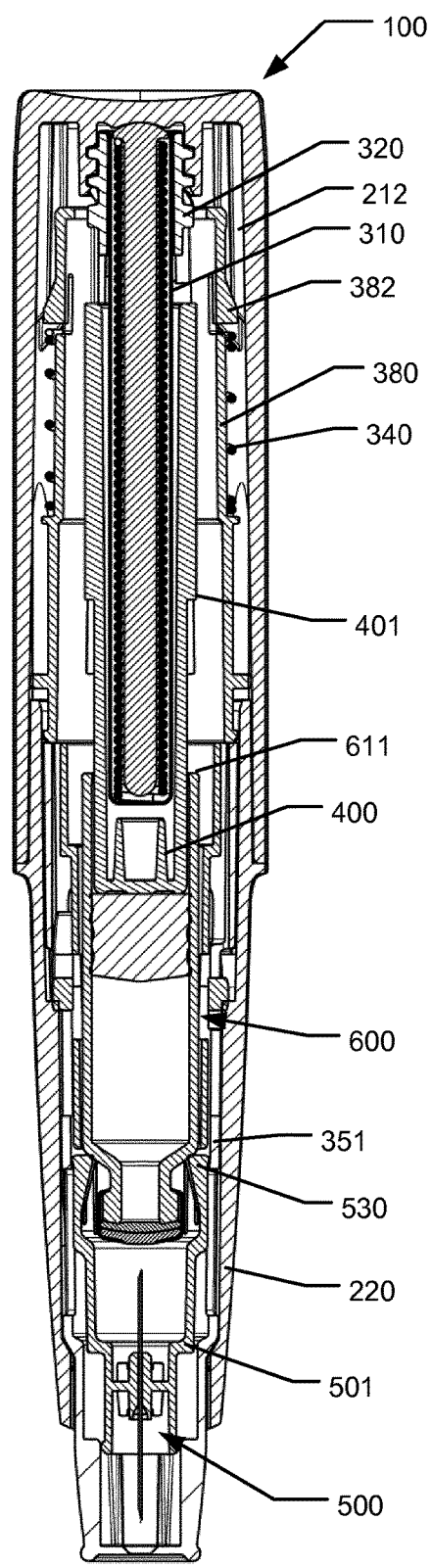
Figure 1C:
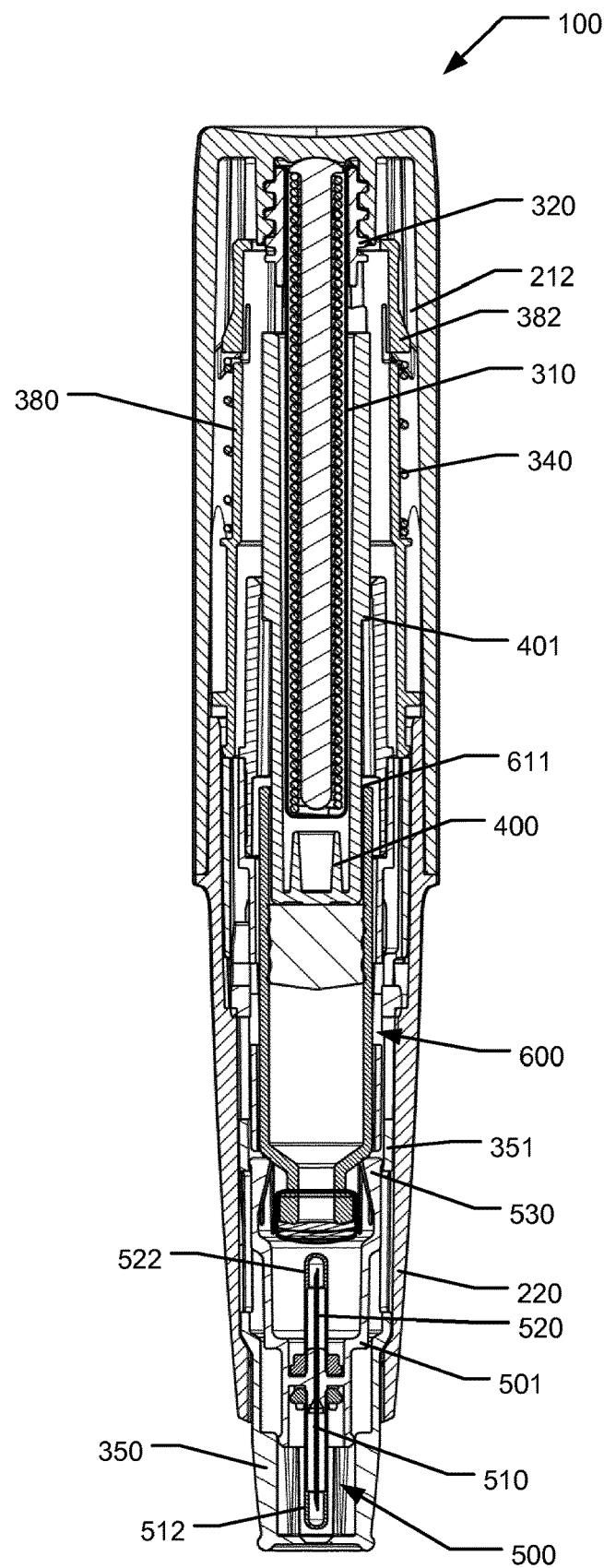
Figure 2A:
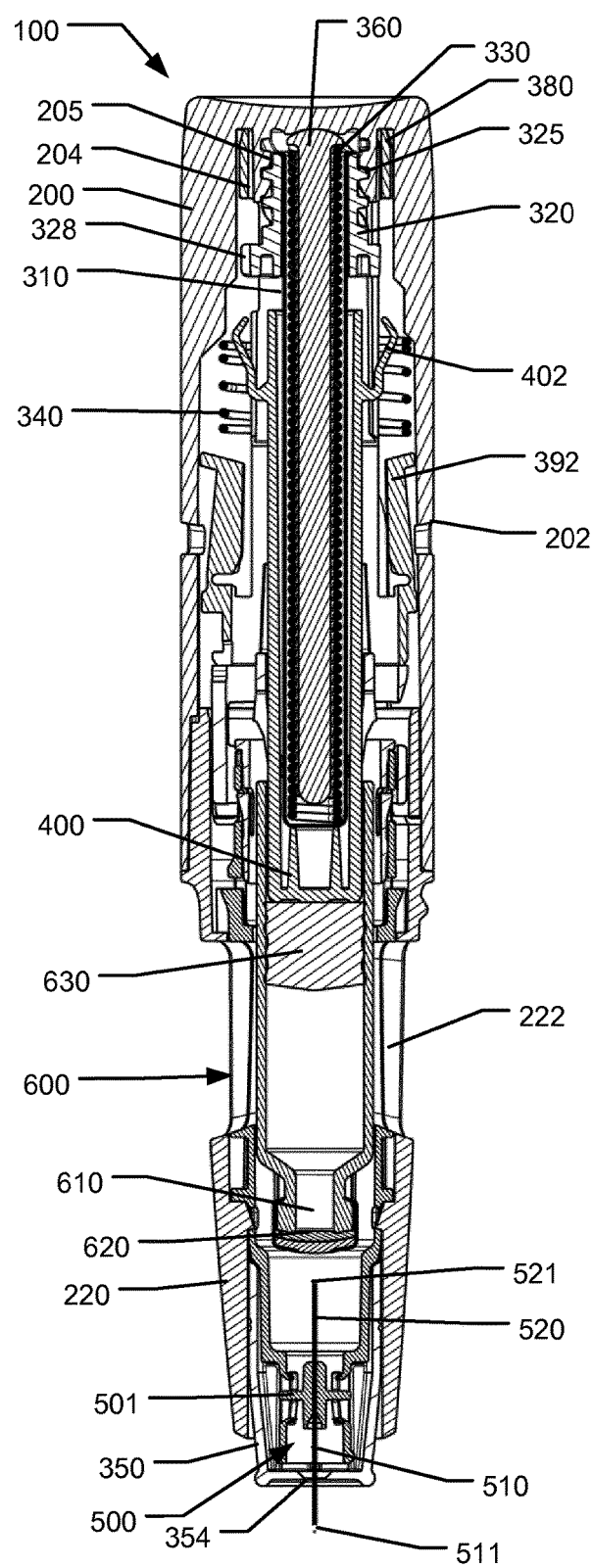
Figure 2B:
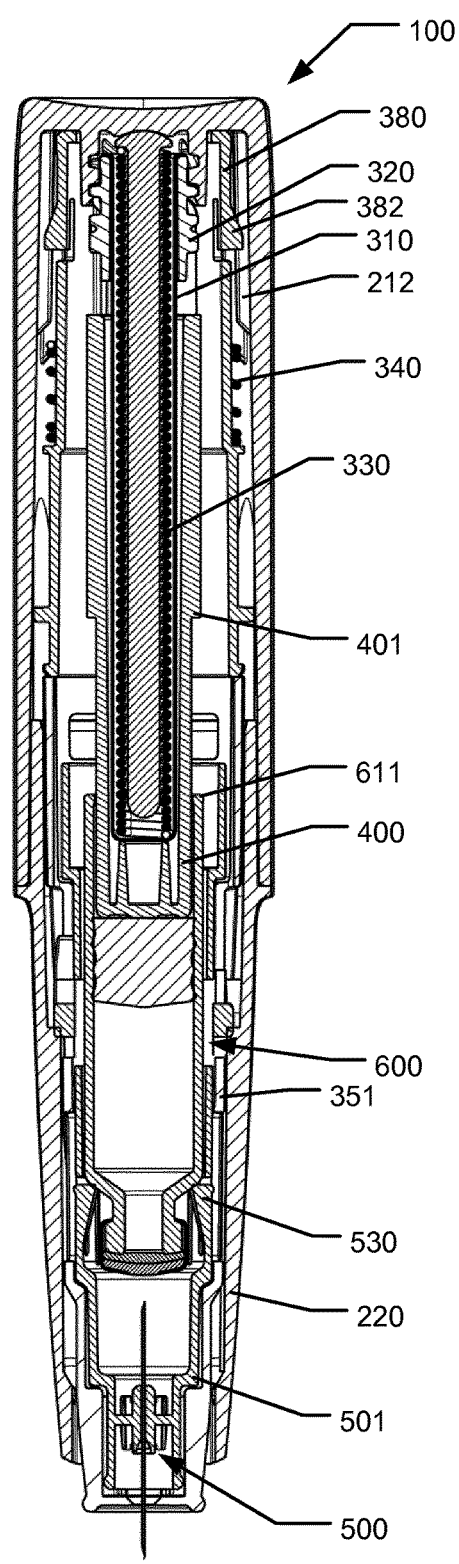
Figure 2C:
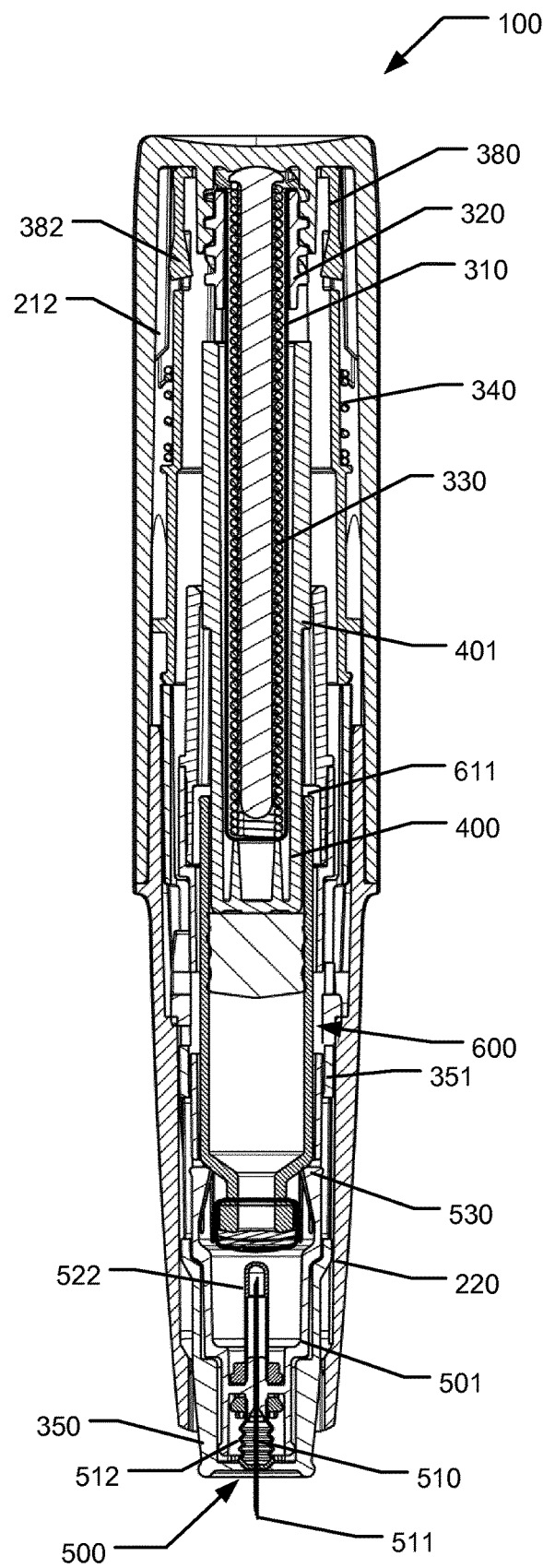
Figure 3A:
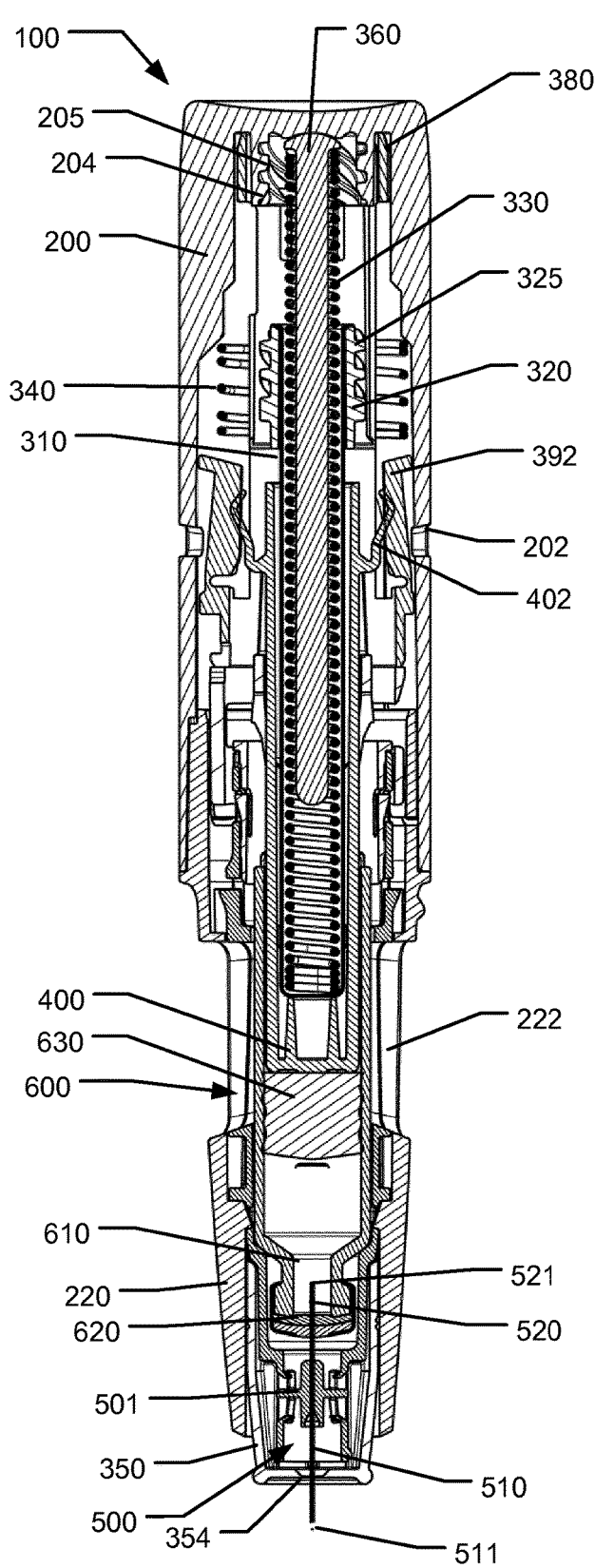
Figure 3B:
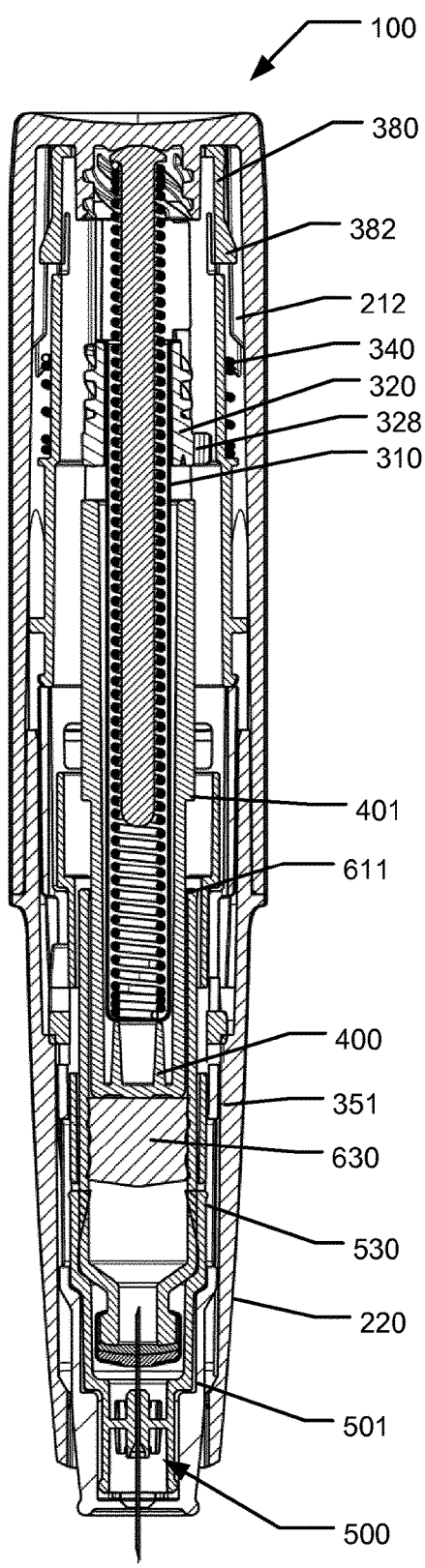
Figure 3C:
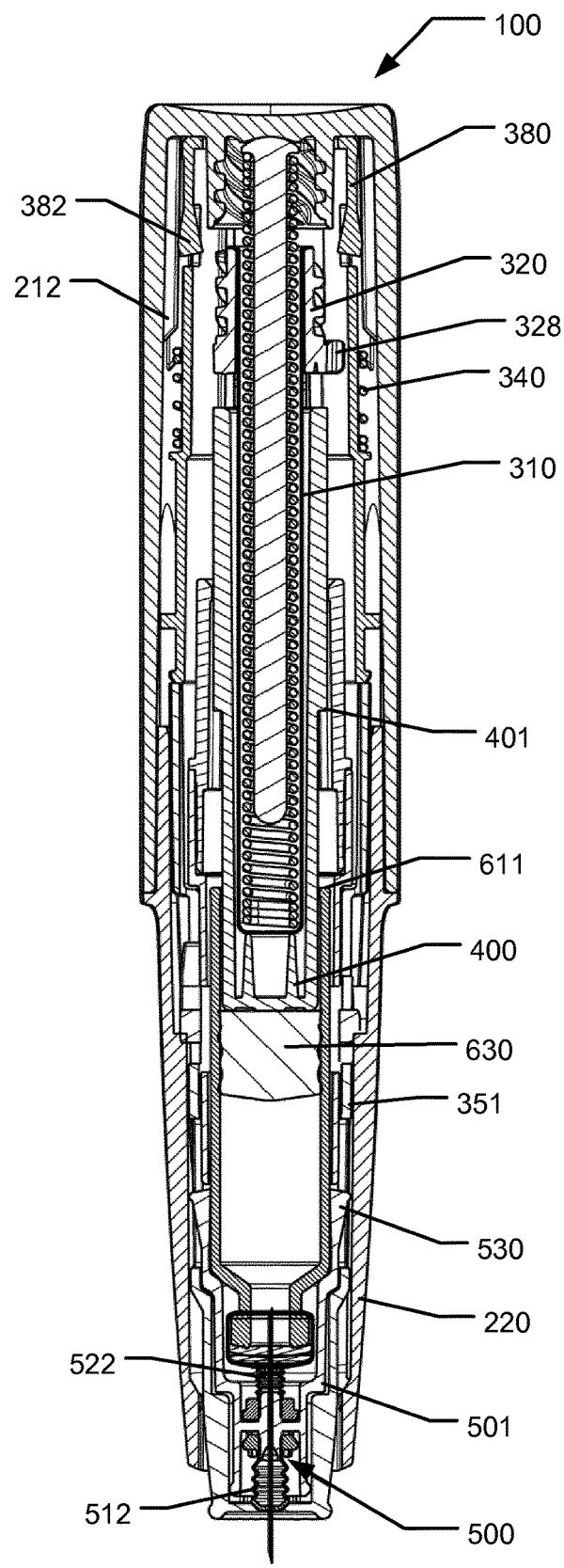
Figure 4A:
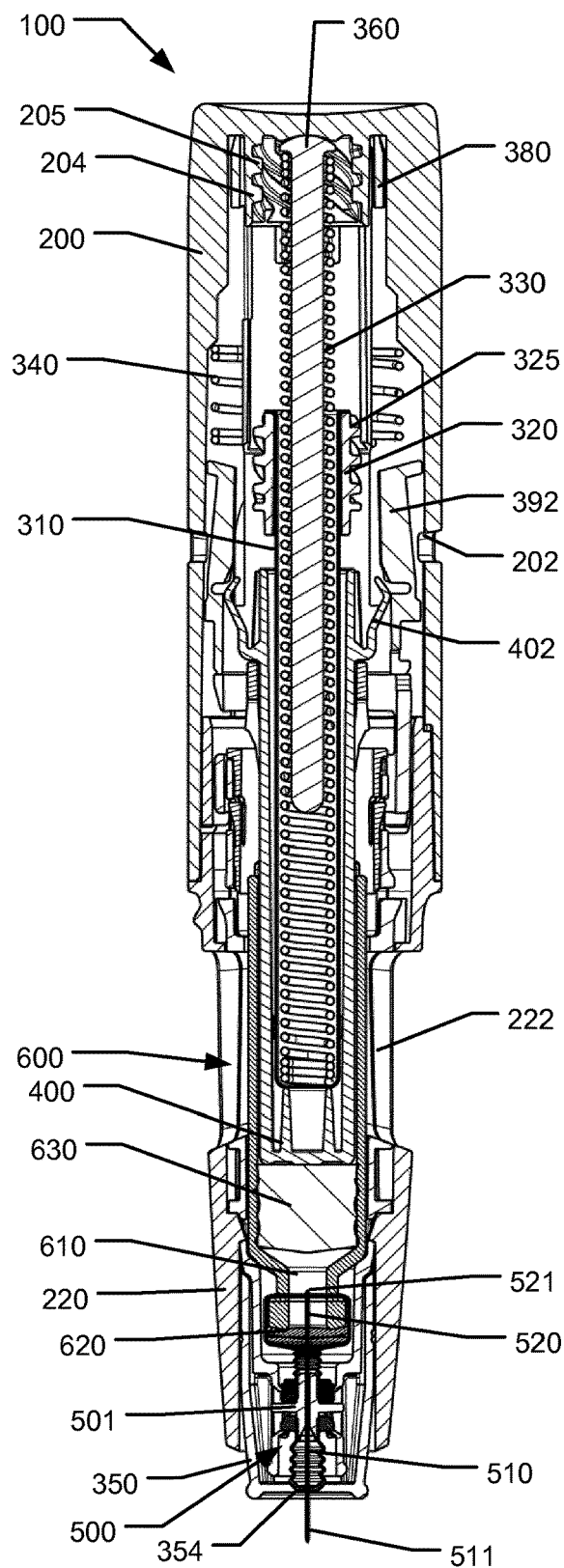
Figure 4B:
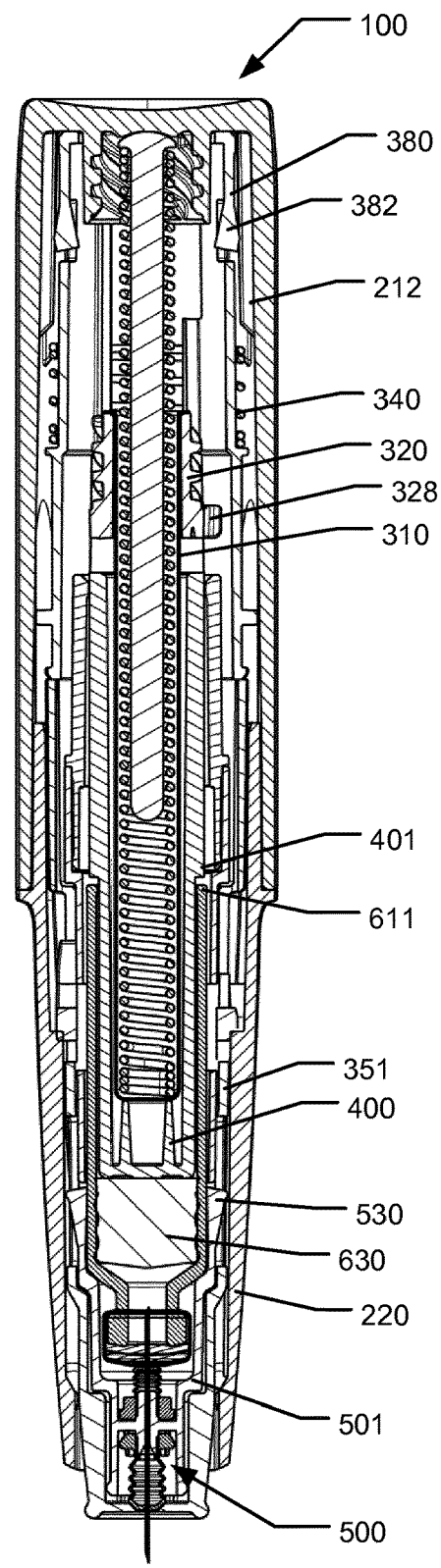
Figure 5A:
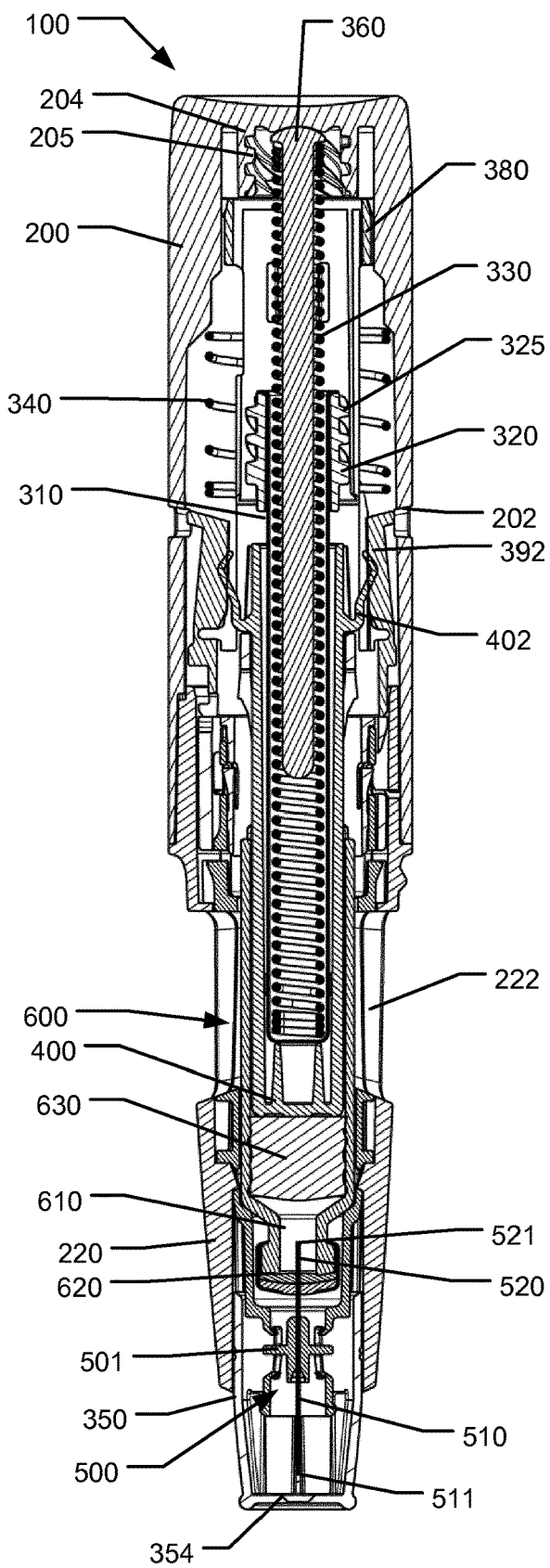
Figure 5B:
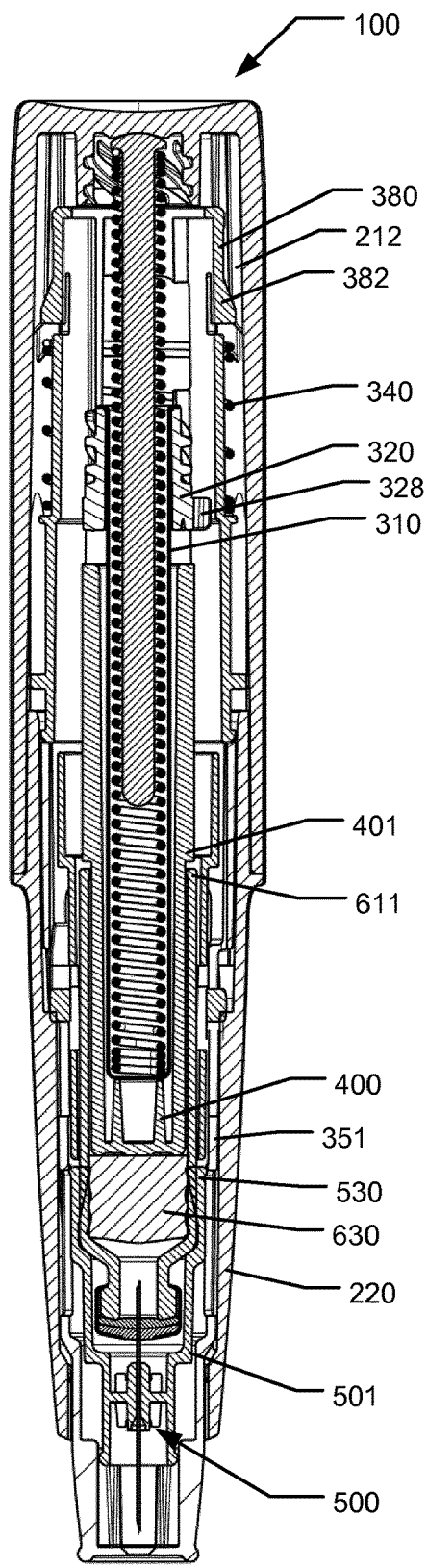
Figure 5C:
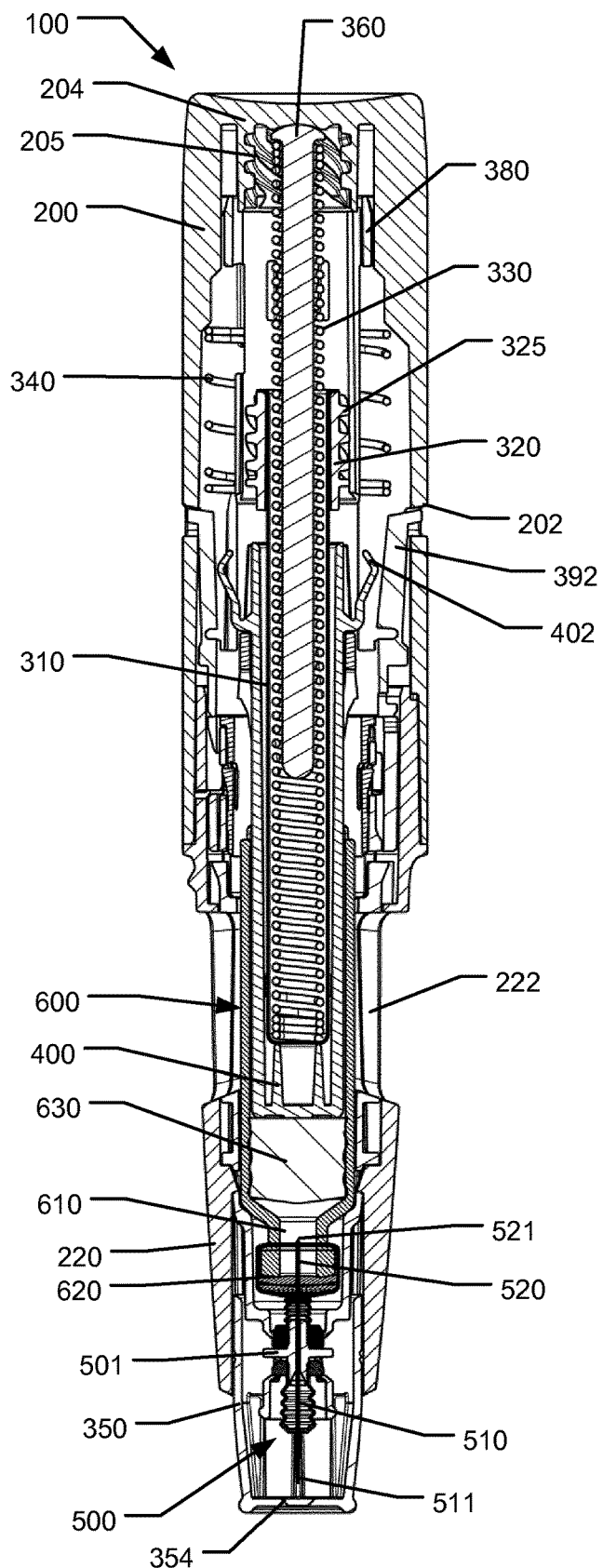
Figure 6:
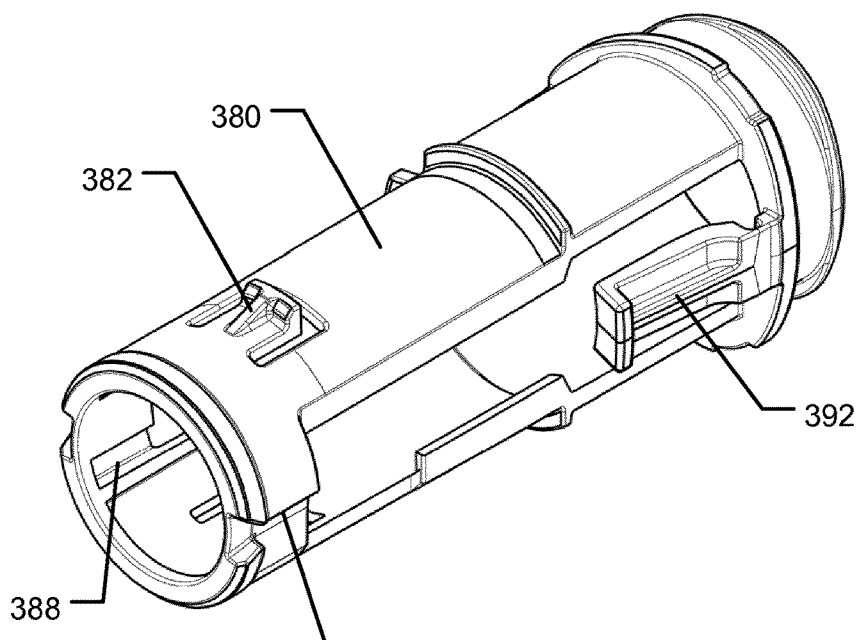
Figure 7:
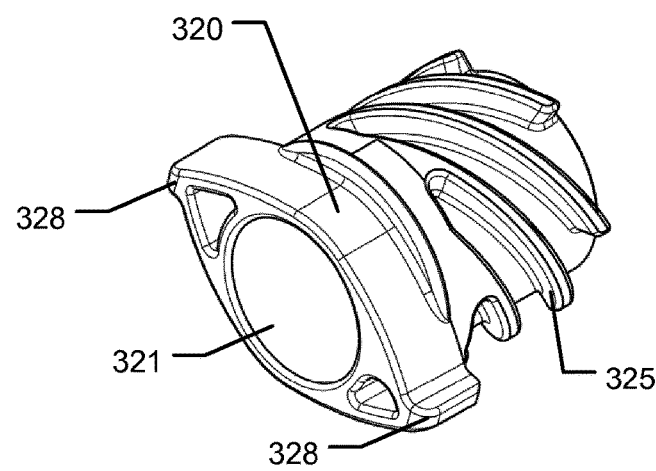
Figure 8:
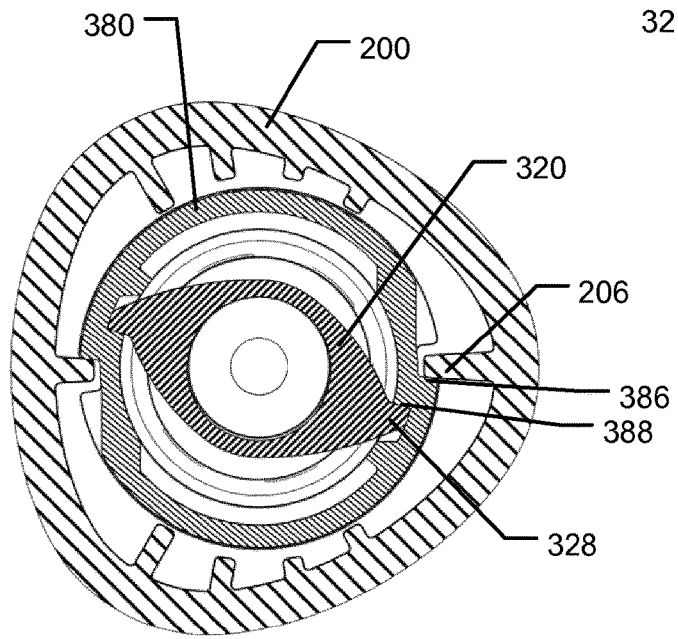
Figure 9A:
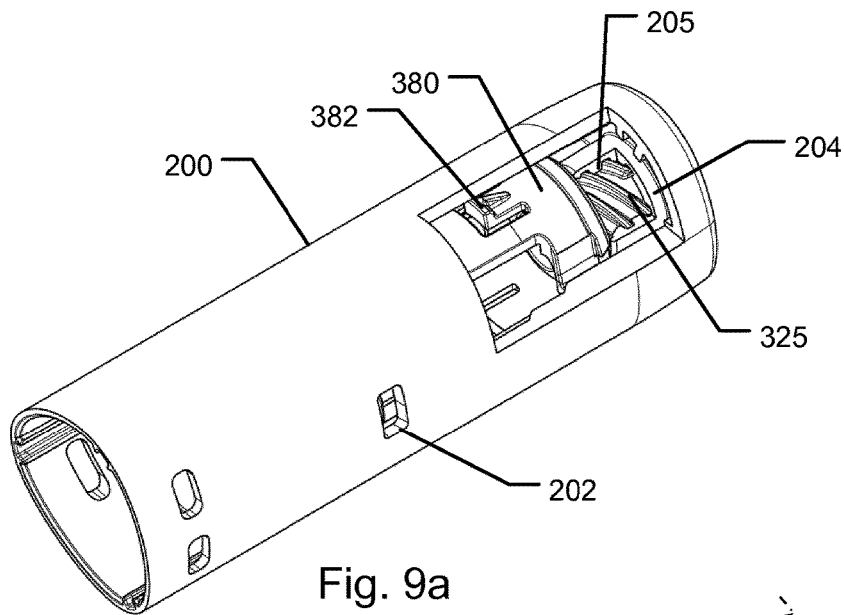
Figure 9B:
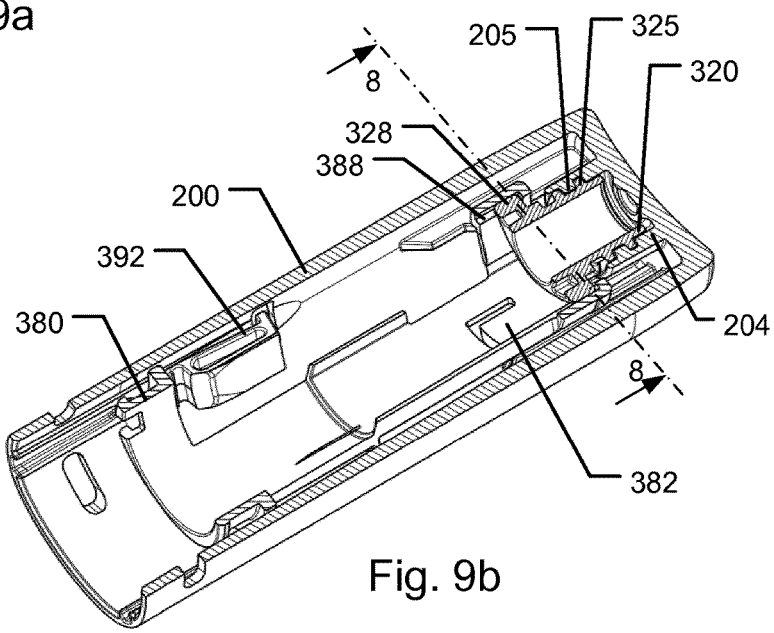
Figure 9C:
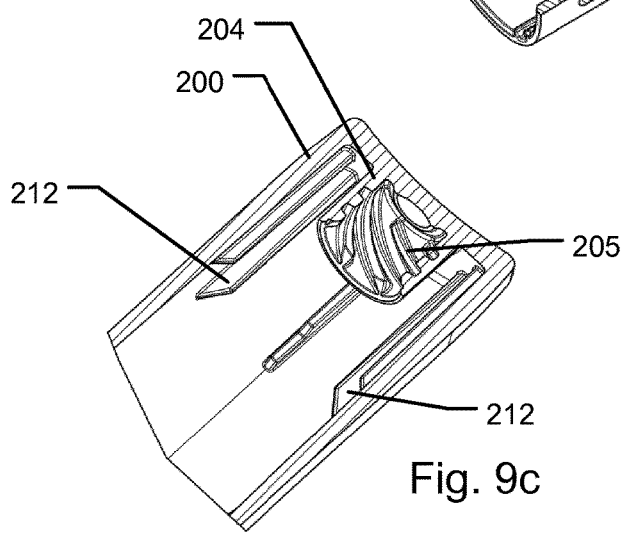
Figure 10A:
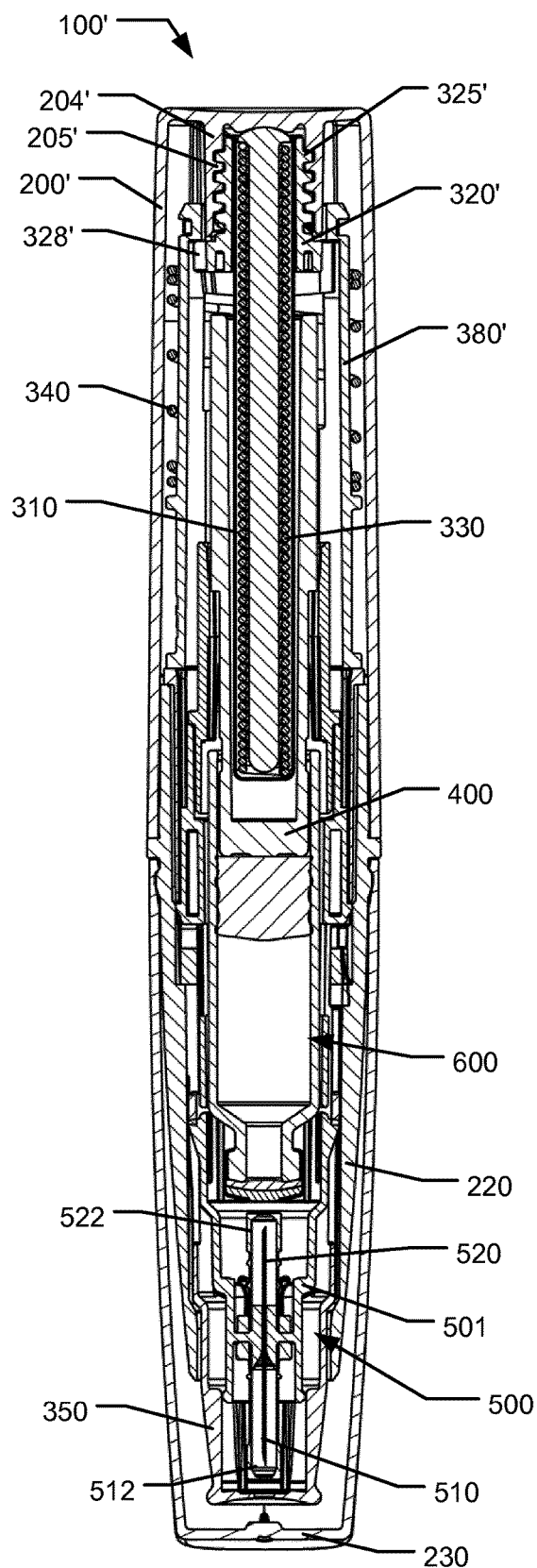
Figure 10B:
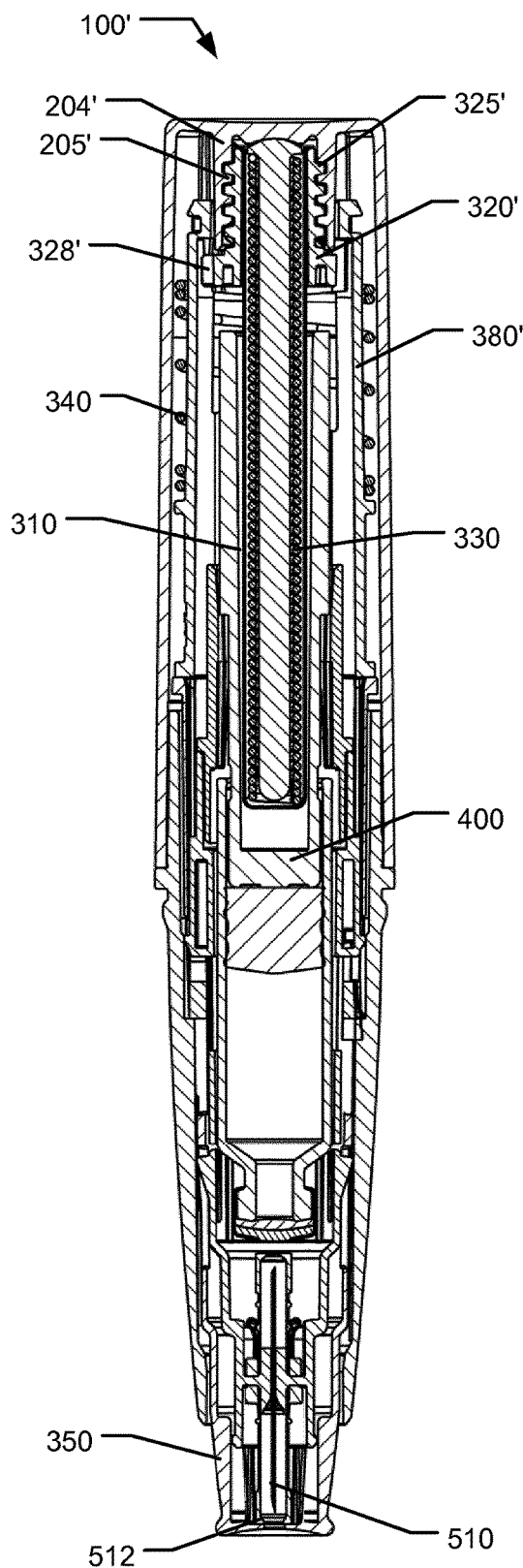
Figure 10C:
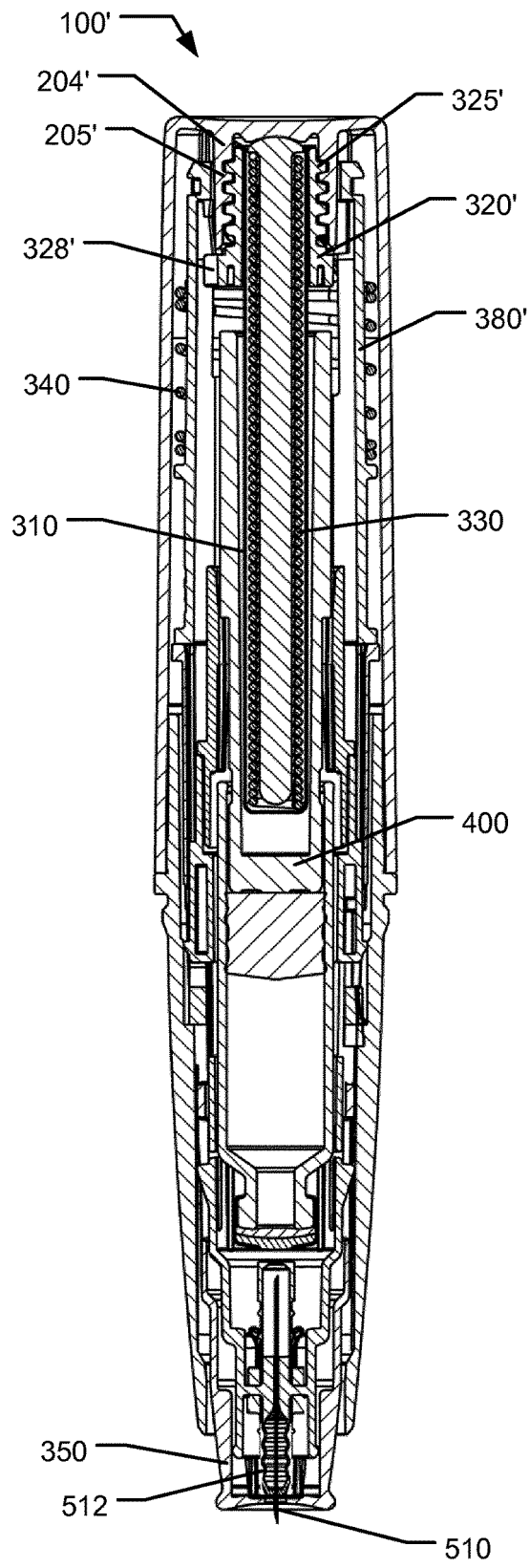
Figure 10D:
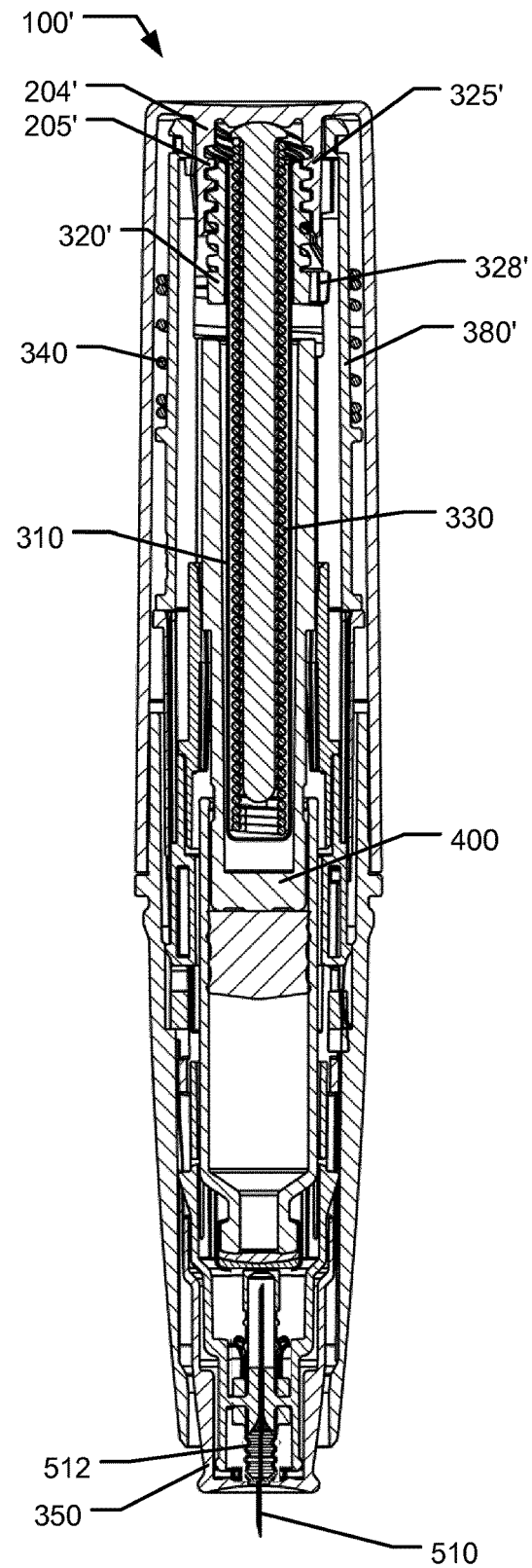
Figure 11A:
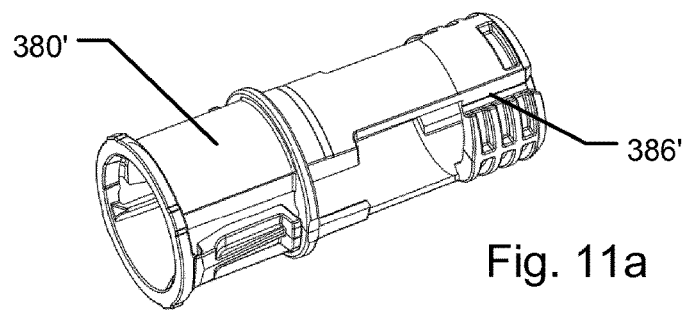
Figure 11B:
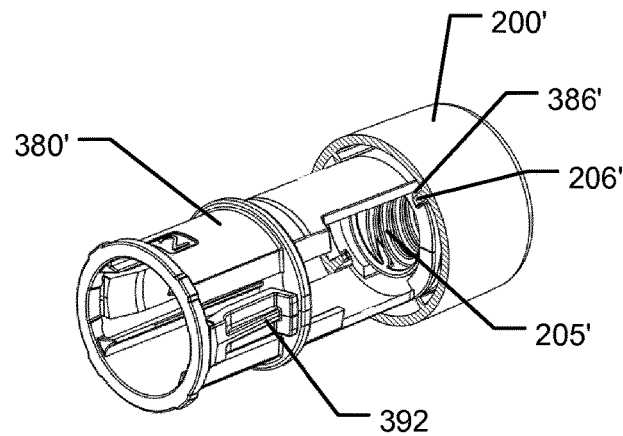
Figure 11C:
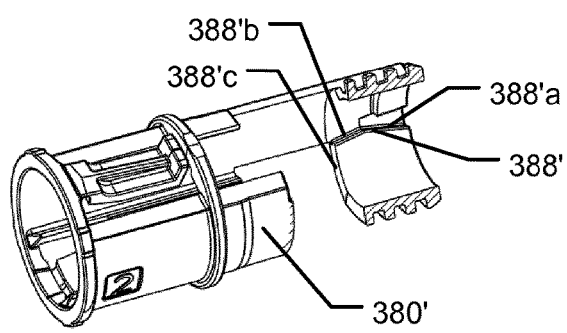
Figure 11D:
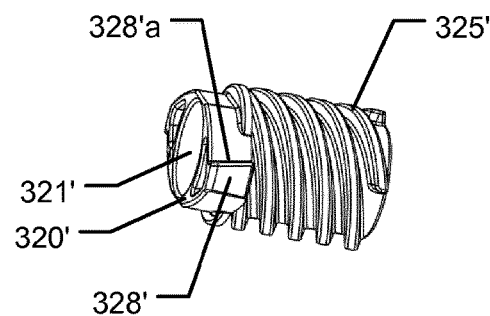
Figure 12A:
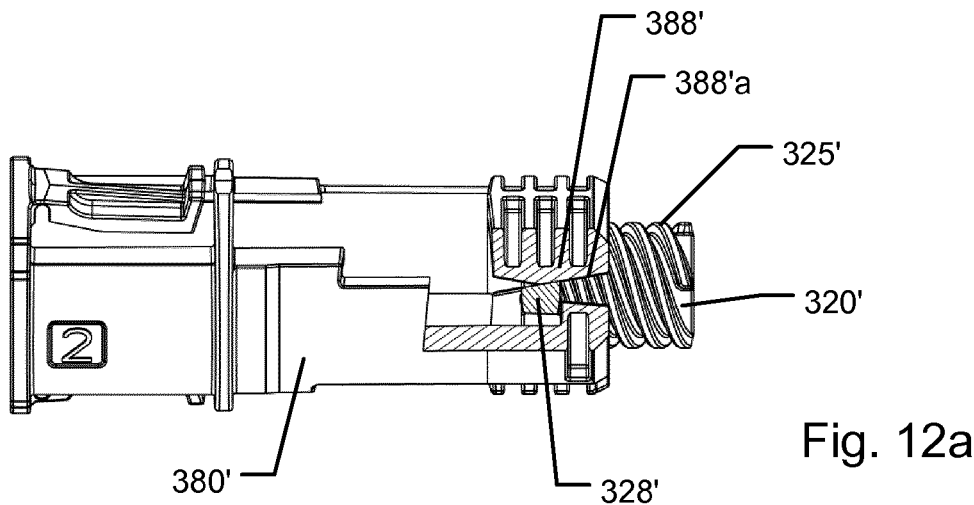
Figure 12B:
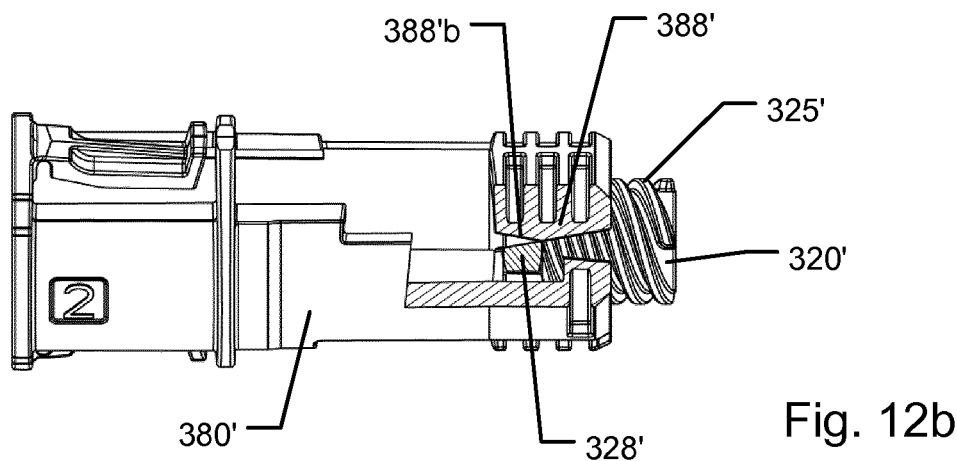
Figure 12C:
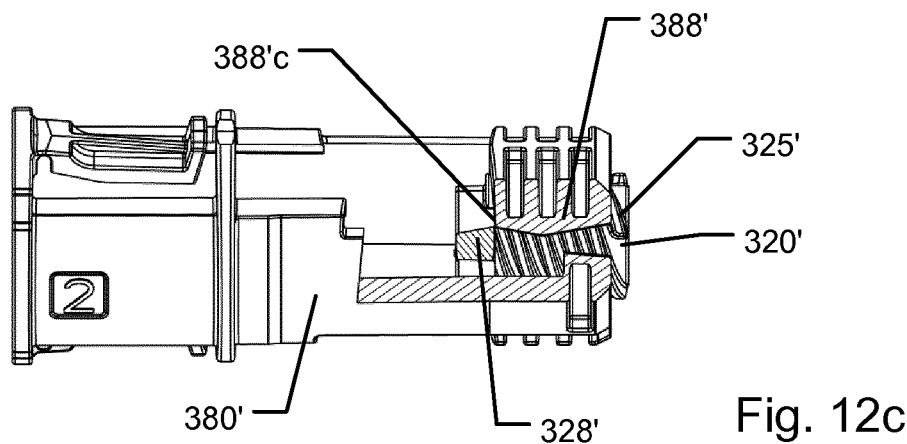
Figure 13A:
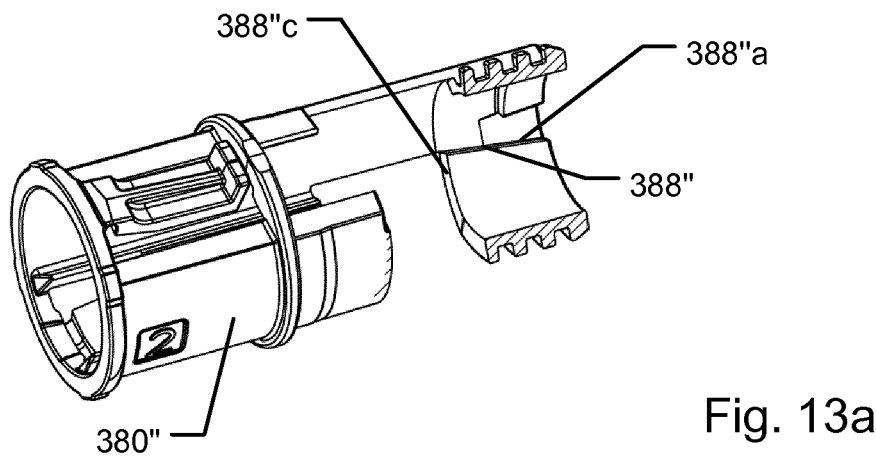
Figure 13B:
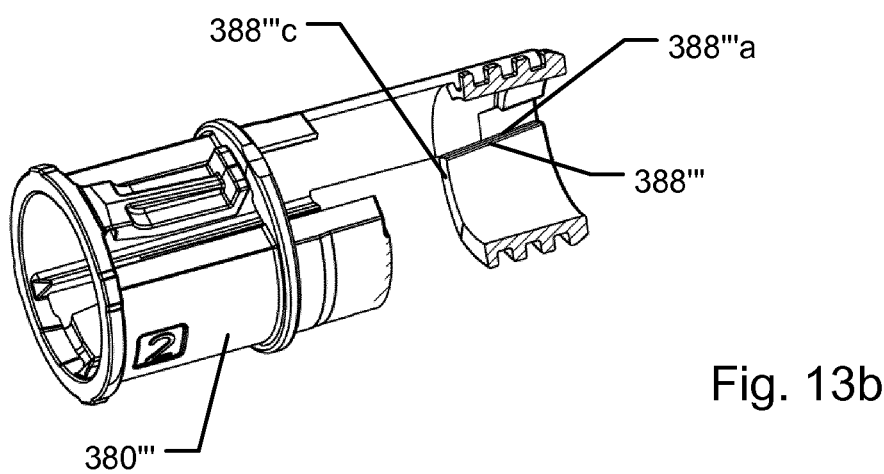
Figure 14:
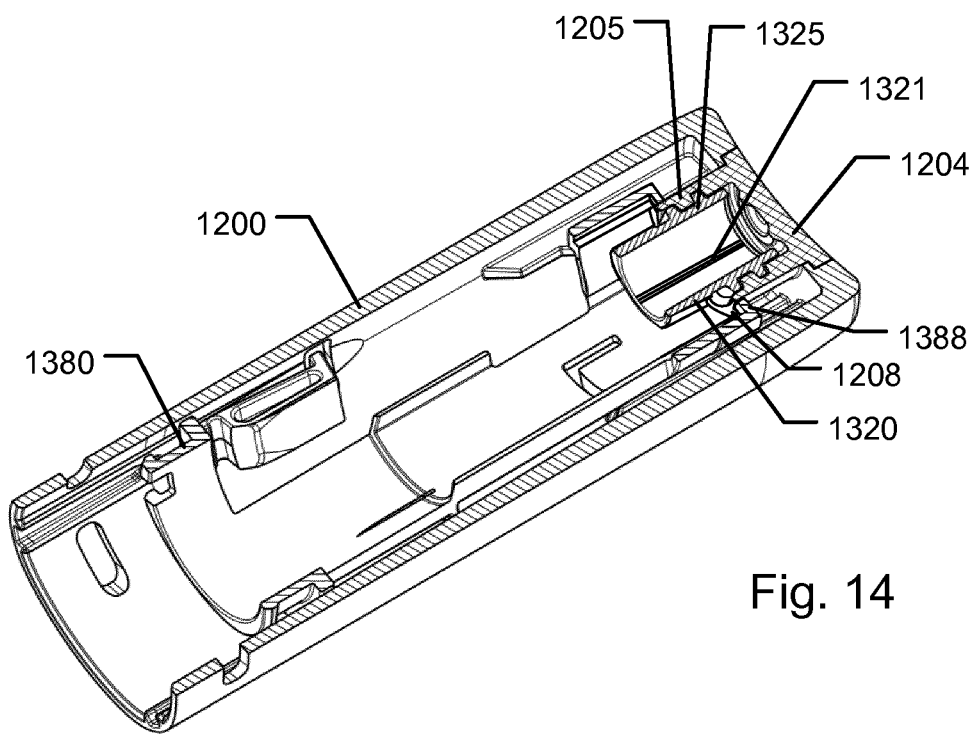

The invention will now be described in further detail with reference to the drawings in which:

FIGS. 1a, 1b and 1c show sectional front and side views of an exemplary embodiment of an autoinjector 100, the injection device being in an initial shielded state, FIGS. 2a, 2b and 2c show sectional front and side views of the device 100 illustrating a state where a front needle fully protrudes from a needle shield, FIGS. 3a, 3b and 3c show sectional front and side views of the device 100 illustrating a state where the cartridge has been connected to the needle for fluid delivery and wherein expelling has been initiated, FIGS. 4a and 4b show sectional front and side views of the device 100 illustrating a state where a predetermined dose of medicament from the cartridge has been expelled, FIGS. 5a, 5b and 5c show sectional front and side views of the device 100 illustrating a state where the needle shield has returned to the shielded state, FIG. 6 is a detailed perspective view of a trigger element of the device 100, FIG. 7 is a detailed perspective sectional view of a plunger release element of the device 100, FIG. 8 shows a cross sectional view of trigger components of the injection device 100, FIG. 9a is a partly cut perspective view of a top housing section of the injection device 100, FIG. 9b is a cross sectional perspective view of the trigger components of the injection device 100, FIG. 9c is a partly cut cross sectional perspective view of the proximal part of the housing section 200, FIG. 10a shows a sectional side view of an exemplary embodiment of an autoinjector 100' of a first type, the autoinjector being in an initial storage state, FIG. 10b shows a sectional side view of autoinjector 100', the autoinjector being in a state just prior to triggering, FIG. 10c shows a sectional side view of autoinjector 100', the autoinjector being in a state where the needle shield assumes a triggering position, FIG. 10d shows a sectional side view of autoinjector 100', the autoinjector being in a state just subsequent to trigger release where the needle shield assumes a collapsed position, FIGS. 11a through 11d show representations of a modified trigger element, a modified top housing section and a modified plunger release element, FIGS. 12a-12c show schematic representations of a trigger element and a plunger release element in different states, FIGS. 13a and 13b show partly cur perspective views of further embodiments of a trigger element, and FIG. 14 shows a schematic representation of the main components for an alternative trigger release mechanism of an autoinjector of a second type.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

The following is a description of an exemplary embodiment of a medical injection device 100 for administering a pre-determined amount of a liquid medicament. The device 100 is an autoinjector configured for expelling a dose of a drug in a single administration whereafter the device 100 is ready for disposal. FIGS. 1a through 5c show various states of the injection device 100 during operation thereof with different views offering a detailed assessment of the operating principle.

It is to be noted that the group of FIGS. 1c, 2c, 3c, 4a, 4b and 5c depicts a few more components than shown in the remaining illustrations spanning the series of FIGS. 1a-5c. Furthermore, having regard to elements that during operation will deform into a deflected state, the first mentioned group of figures illustrates the true operational state of the deflected elements more correctly than the corresponding elements in FIGS. 1a-5c.

Injection device 100 includes a generally tubular housing that extends along a central longitudinal axis. The housing forms a base that includes a lower housing section 220 arranged at a distal end of the device and a top housing section 200 arranged at a proximal end of the device. The lower housing section 220 and the top housing section 200 are joined to each other to form an enclosure to accommodate a medicament cartridge 600 having an elongated body 605. As will be later discussed, the base is associated with a base thread 205.

Injection device 100 may further include a removable protective cap (not shown) that attaches to a distal end of the device 100 to protect a needle end of the device 100. The lower housing section 220 includes two opposing windows 222. When the cap has been removed from the device 100, the windows 222 allow visual inspection of the medicament contained within the device 100. In addition, windows 222 allow a user of the device to determine whether or not the device 100 has been used for an injection by inspecting the presence or the location of a piston of a medicament cartridge 600, or alternatively part of a plunger arrangement, arranged within the housing. In the shown embodiment top housing section 200 is for manufacturing reasons formed as an element separate from but permanently fixed to lower housing section 220 but may in alternative embodiments be formed integral with lower housing section 220.

FIGS. 1a, 1b and 1c show front and side sectional views of the device 100 after the protective cap has been removed but in a condition prior to the administration operation. Shown protruding from the distal end of the lower housing section 220 is a needle shield 350 which is arranged coaxially and slidable relative to lower housing section 220. Needle shield 350 is slidable relative to the housing between a distal extended position where a front end of a needle assembly 500 arranged internally in lower housing section 220 is in a shielded state and a second proximal collapsed position where a front needle end of the needle assembly 500 protrudes through an aperture 354 arranged in the central part of a distal wall surface of the needle shield 350.

The injection device 100 is configured for being triggered to inject a dose when the needle shield 350 is moved from the distal extended position towards the collapsed position. The protective cap, when attached to the lower housing section 220, prevents the needle shield 350 from being manipulated and thereby prevents premature triggering of the injection device 100.

Lower housing section 220 accommodates a medicament filled cartridge 600 having an outlet 610 covered by a cartridge septum 620 adapted to be pierced by a needle for establishing fluid communication with the cartridge interior and having a slidably arranged piston 630. Piston 630 is driveable towards the outlet 610 when a needle pierces the cartridge septum 620 in order to dispense medicament from the cartridge 600. The dispensing is controlled by an expelling assembly. Cartridge 600 is arranged movable with respect to the lower housing section 220 from a proximal storage position to a distal active position.

Distally in the lower housing section 220 is a needle unit in the form of a needle assembly 500 arranged in an initially separated configuration with respect to cartridge 600. In the shown embodiment, needle assembly 500 includes a needle cannula having a front needle 510 and a rear needle 520 respectively protruding in the distal and proximal directions from a needle hub 501. Both front needle 510 and rear needle 520 include pointed tips 511 and 521 for respectively piercing the skin of a user and the cartridge septum 620.

As shown in FIG. 1c, the needle assembly 500 furthermore may include a front cover 512 and a rear cover 522 forming sterility sheaths for the front needle 510 and rear needle 520 respectively. Each of the front and the rear covers may be formed as a rubber sheath which is penetrable by the pointed tip portions of the needle 511/521 when the cover 512/522 is forced towards the needle hub 501. Prior to use of the device 100, each of the two covers 512/522 assumes the extended position in which the cover seals of the respective one of the front 510 and rear needle 520. The front and rear covers may be attached to the hub 501 either by gluing, welding, interference fit, a separate mounting element, or by corresponding means.

The needle cannula may be attached to the hub 501 by gluing, interference fit or similar joining process. In the embodiment shown, the hub 501 is an element separate from the housing but may in alternative embodiments be formed as a part of the housing 200/220. Hub 501 is formed as a generally tubular structure which extends proximally along the cartridge and even further to a position proximal to the cartridge. In this way the hub 501 supports the cartridge 600 along an exterior cylindrical wall of the cartridge. As such, the hub 501 is designed to perform as a cartridge holder relative to which the cartridge 600 is allowed to axially slide between the proximal storage position and into the distal active position.

In the shown embodiment, the needle hub 501 and hence the needle cannula is axially mounted relative to the housing of the device 100 so that the needle cannula follows axial movements of the housing when the housing is moved relative to the needle shield 350.

In the shown embodiment, the needle shield 350 is formed as a generally tubular member having a distal face arranged to initially cover the front needle 510 and the front cover 512. The needle shield 350 is mounted slidable relative to the lower housing section 220 allowing limited axial movement by a predefined axial distance.

The needle shield 350 cooperates with a trigger element 380 which is located proximally to the needle shield 350. Trigger element 380 is also formed as a generally tubular element and extends axially in the proximally direction from the needle shield to a location close to the proximal end of top housing section 200. In the assembled state of the device 100, the needle shield 350 and the trigger element 380 perform as a single entity, i.e. the movement of trigger element 380 follows axial movement of the needle shield 350. Hence the trigger element 380 is movable from a distal end position corresponding to the extended position of the needle shield 350 to a proximal end position corresponding to the collapsed position of the needle shield 350. In the shown embodiment, each of the needle shield 350 and the trigger element 380 are mounted in a way that prevents rotational movement relative to the housing 200/220.

A needle shield spring 340 is arranged between the housing section 200 and the trigger element 380. The trigger element 380 is urged in the distal direction by means of the needle shield spring 340 so that when no external applied force is exerted on the needle shield, the needle shield assumes its distal extended position which is shown in FIGS. 1a, 1b and 1c. In this position a stop geometry on trigger element 380 and/or needle shield 350 prevents the two components from moving further in the distal direction. When an externally applied force is exerted on the needle shield 350 for moving the needle shield in the proximal direction relative to the housing, such as when device 100 is pressed with the needle shield against an injection site, the externally applied force acts counter to the force provided by the needle shield spring 340 resulting in the needle shield 350 and the trigger element 380 being forced to move in the proximal direction. When the needle shield 350 assumes the proximal collapsed position a proximal end surface of the trigger element 380 prevents the trigger element and the needle shield 350 from moving further proximally relative to the housing (cf. FIGS. 2a-2c).

As the device 100 is removed from the injection site, the needle shield 350 will move distally due to the force from the needle shield spring 340. After an injection has been performed, as the needle shield 350 reaches its distal position again, as shown in FIG. 5c, it will be locked in this position to render the needle shield inoperable (to be further explained below).

The needle assembly 500 is arranged at the distal end of the lower housing section 220, such that the needle shield 350 completely covers the needle assembly when the needle shield is in its extended position. When the needle shield 350 is in its proximal collapsed position, the front needle 510 protrudes through the aperture 354 of needle shield 350.

As indicated in FIG. 1b, the cartridge 600 is maintained in its proximal storage position by means of two resilient arms 530 that extend radially inwards from the needle hub 501. In the initial state shown in FIG. 1b, the resilient arms 530 assume a position where they support and retain a neck portion of the cartridge 600 to prevent the cartridge from moving in the distal direction. The resilient arms 530 are adapted to flex radially outwards when sufficient force acting to move the cartridge 600 in the distal active position is exerted on cartridge 600. However, in the initial state where the needle shield 350 assumes its distal extended position, a blocking geometry 351 of the needle shield 350 encircles the resilient arms 530 to prevent them from flexing outwards and thus prevents the cartridge 600 from being moved distally. As will be described later, the blocking geometry 351 is configured to move axially when the needle shield 350 is moved into its proximal collapsed position making room for the resilient arms 530 to be flexed radially outwards.

The expelling assembly of injection device 100 is based on a plunger arrangement that is driven in the distal direction along the central longitudinal axis of the device for advancing the piston 630 to thereby expel a dose from the cartridge 600. The plunger arrangement in the shown embodiment includes a drive ram 310 and a spacer member 400. In device 100 an actuator 330 is arranged in the proximal part of the device providing a stored energy source for exerting a distally directed force on drive ram 310. Spacer member 400 is a generally tubular member that is positioned between drive ram 310 and the piston 630 of the cartridge 600. Spacer member 400 acts as an intermediary member for transferring a force exerted by the drive ram 310 on the piston 630 for forwarding the piston in the distal direction. Spacer member additionally serves as a lock activator for a shield lock and for generating click sounds as the spacer member is advanced.

The actuator is provided in the form of actuating spring 330 that in the shown embodiment is provided as a pre-stressed helical compression spring. The actuating spring 330 is energized by straining the compression spring during manufacture of the device. The drive ram 310 is furthermore hollow to allow the actuating spring 330 to be positioned within the drive ram 310. A guiding element 360 arranged internally in actuation spring 330 assists in guiding the actuation spring 330 to prevent it from bending sideways. Guiding element 360 provides at its proximal end a seat portion arranged to act as a seat for supporting the proximal end of actuation spring 330.

The spacer member 400 is formed with stop surfaces 401 positioned a predetermined distance from the distal end of spacer member 400 to cooperate with the rear end 611 of the cartridge 600 to thereby define a precise end of stroke position for the piston 630 inside cartridge 600. As the piston 630, during filling of the cartridge 600, can be accurately positioned with respect to the rear end 611 of the cartridge 600, the exact volume of an expelled dose can be accurately controlled by utilizing the stop surfaces 401 hitting the rear end 611 of cartridge 600 at completion of the expelling operation.

In the embodiment shown, spacer member 400 and a cooperating member associated with the housing may further include one or more pairs of click generating elements such as protrusions adapted to cooperate with click arms to generate click sounds during and/or at the completion of the injection.

As mentioned, in the shown embodiment, the actuator in the form of a pre-stressed actuation spring 330 urges the drive ram 310 in the distal direction. In the unactivated state of the injection device 100, a plunger release element 320 associated with drive ram 310 cooperates with the top housing section 200 and the trigger element 380 to retain the drive ram 310 in an initial axial position against the force of the actuation spring 330. Upon activation of the expelling assembly, i.e. by operating the trigger element, the plunger release element 320 is released allowing the drive ram 310 to thrust forward for providing a distally directed force on the piston 630 via the spacer member 400.

Alternatively to using a pre-stressed spring which is compressed during manufacture of the device, other embodiments of autoinjectors may include a mechanism for compressing the spring as an initial procedure when putting the device into use. Also, the actuator may in other embodiments be formed to include a torsion component, where the actuator is pre-stressed to exert a torsion force for driving forward a rotational drive of the expelling assembly. Alternatively, the actuator may be in the form of a compressed medium such as a gas. Still alternatively, the actuator may include a gas generator such as an electro-chemical cell.

The drive ram 310 of the plunger arrangement is provided as a deep-drawn metal tube extending along the central longitudinal axis and defining a closed distal end and an open end portion having a collar extending radially outwards at its proximal end. The plunger release element 320 is arranged at the proximal end of the drive ram 310 to encircle the drive ram 310. Plunger release element 320 has an axial bore 321 defining a circumferential collar that rests against the collar of the drive ram 310 to prevent the drive ram 310 from moving distally relative to plunger release element 320. In the shown embodiment, the plunger release element 320 is freely rotatable relative to drive ram 310 and may, after triggering and soon after the cartridge 600 reaches the distal active position, slide axially forward relative to the drive ram 310. In the shown embodiment the plunger release element 320 is rotatable around a first rotational axis which is coaxial with the central longitudinal axis mentioned above.

Shown in greater detail on FIGS. 9a-9c plunger release element 320 defines a thread 325 that engages a thread 205 associated with the housing section 200 when the device 100 is in the initial state prior to triggering. A releasable lock serving as a retaining function acts to prevent relative rotation between the plunger release element 320 and the housing section 200, thereby maintaining the drive ram 310 in the initial axial position.

In the shown embodiment, the releasable lock is provided by the trigger element 380 which in the initial distal position prevents relative rotational movements, induced by the actuating spring 330, between the plunger release element 320 and the housing section 200. As shown in FIGS. 6 and 8 axial tracks 386 of trigger element 380 are configured to be engaged by respective axial ribs 206 of top housing section 200 preventing the trigger element 380 from rotation relative to the housing 200/220 but enabling axial displacement. In the shown embodiment, two radially outwards extending protrusions 328 of plunger release element 320 are adapted to engage corresponding axial tracks or ribs 388 extending radially inwards on an inner surface of trigger element 380 (see FIGS. 5, 6 and 7). The axial tracks 388 each has a limited axial length defining circumferential neighbouring areas that are open at a location at the distal end of axial tracks 386. When sufficient axial displacement of the trigger element 380 relative to the plunger release element 320 has been obtained, rotation of plunger release element 320 is enabled. But in the initial state prior to triggering, as long as the trigger element 380 is situated distally relative to a pre-defined trigger release position, the plunger release element 320 is prevented from rotating. The trigger release position of the trigger element 380 is located at a point in close proximity but distally to the proximal end position of the trigger element 380.

As long as the plunger release element 320 is prevented from rotating relative to the housing the threaded engagement between the thread 325 of the plunger release element 320 and the thread 205 of the housing prevents the plunger release element 320 from being moved axially. Hence, prior to activation of the expelling assembly, the drive ram 310 is also prevented from being moved in the distal direction as long as the trigger element 380 is located distal to the trigger release position. In the shown embodiment, thread 325 and thread 205 are dimensioned to provide large surface areas to take up the force from actuator 330, enabling the use of plastic materials for the threaded components thereby providing low-friction engagement between components that operates during triggering.

In the shown embodiment, the lead of the threaded connection 325/205, the length of the threads and the dimensions of the engagement between the protrusions 328 and the axial tracks 388 are so configured that, upon displacement of the trigger element 380 towards the trigger release position, once the plunger release element 320 has been released for rotation and thus rotated slightly, the protrusions 328 cannot reengage the axial tracks 388. Hence, once the expelling assembly has been activated by exerting a force on the needle shield 350 for triggering the device, in case of a potential release in the force exerted on the needle shield, the distal movement of the drive ram 310 cannot be interrupted, i.e. the drive ram 310 will continue its distal movement until the intended end of dose position defined by the elements 401/611.

FIG. 9a shows a partly cut perspective view of the top housing section 200 wherein the trigger element and the plunger release element 320 are visible. The plunger release element 320, the trigger element 380 and the top housing section 200 together form the main trigger components of the device. For clarity, the depicted view only shows selected components of the injection device 100 in the initial state prior to triggering but wherein additional components such as the actuating spring 330 and the drive ram 310 are omitted. Visible is also the engagement between the thread 325 of the plunger release element 320 and the thread 205 of base component 204 defined by housing section 200. Base component 204' is similarly shown in FIGS. 10a, 10b, 10c, and 10d. FIG. 9b shows the trigger components in a sectional perspective view.

Referring back to FIG. 1c and FIG. 6, the trigger element 380 includes a pair of resilient arms 392 that partly constitutes a needle shield lock which renders the needle shield 350 permanently arrested when the needle shield, subsequent to finalisation of an injection, is returned to the extended position.

Each of the resilient arms 392 are configured to be flexed radially outwards away from a passive unbiased configuration and into a biased active configuration where the needle shield lock is provided. The passive unbiased configuration is best viewed FIG. 1a. Each of the resilient arms 392 forms an outer protrusion that is configured to enter into a corresponding recess 202 formed in housing section 200 when the needle shield 350 is to be arrested.

The said needle shield lock further incorporates a lock activator in form of a pair of thrust arms 402 associated with the plunger. In this embodiment the thrust arms 402 are formed by and extending radially outwards from the spacing member 400. The thrust arms 402 include a resilient section 403 that provides resiliency in the radial direction. When the axial position of the thrust arms 402 corresponds to the axial position of the resilient arms 392, each of the thrust arms 402 cooperates and exerts a radially outwards directed force on a respective resilient arm 392 to force the resilient arm 392 radially outwards. However, the radially outwards force exerted by the thrust arm 402 only moves the resilient arm 392 outwards and into its corresponding recess 202 after the drive ram 310 has reached its end of dose position. When the protrusions of each of the resilient arms 392 do not align axially with its corresponding recess 202, the resilient arm 392 is prevented from moving radially outwards.

The needle shield or the trigger may further comprise a one or more contact surfaces each being resiliently slideable over a respective cooperating ramp surface formed in the housing. Referring to FIGS. 1c, 6 and 9c, in the shown embodiment, the contact surfaces are provided by trigger element 380 as a pair of resilient snap arms 382 that are adapted to deform radially inwards relative to the shown unbiased position. Each snap arm 382 is configured to cooperate with a respective ramp section 212 formed along an internal wall surface in the proximal part of housing section 200. As best viewed in FIG. 2c, each ramp section 212 is formed as an axial extending rib that is provided with a chamfered distal front section allowing the snap arm 382 to be deformed by the chamfered section of ramp section 212, when the trigger element 380 is moved from the distal end position to the proximal end position. The chamfered section of ramp section 212 connects to a ramp segment that continues in the proximal direction with a constant height, i.e. the ramp has an inner ramp surface extending parallel or substantial parallel with the first rotational axis.

When the needle shield 350 is moved from the distal extended position towards the proximal collapsed position, the snap arms 382 of the trigger element 380 and the corresponding ramp sections 212 provide resistance to movement the trigger 380 and thus also resistance to movement of the needle shield 350. Upon applying the autoinjector 100 at an injection site, a high axial force is created initially when the snap arms 382 hits the chamfered sections of ramp sections 212. Thus a high force is required for exertion on the needle shield 350 in order for the snap arms 382 to climb the ramp sections 212. As soon as the snap arms 382 have climbed the ramp sections 212, resulting in the snap arms 382 have been deformed radially inwards, the snap arms 382 travel and slide along the constant height ramp segments as the needle shield 350 is pushed further proximally relative to housing 200/220. This action requires considerable less force to be applied on the needle shield 350 than the initial high force. Hence, in accordance with the snap mechanism incorporating the snap arms 382 and the ramp sections 212, the needle shield displacement will occur in two stages, i.e. a first high force stage and a second low force stage. In the shown embodiment the position that the needle shield assumes between the two stages may be termed the "triggering position". In the shown design, the act of triggering will be virtually impossible to interrupt when the needle shield has passed the triggering position.

It will be appreciated, that the force needed for proximally displacing the needle shield will be largely independent from the force provided by the actuator 330, but will rather be decided by the force of the needle shield spring 340 and the force profile for the interaction between the snap arms 382 and the ramp sections 212. During displacement of the needle shield 350 relative to the housing 200/220, once static friction has been overcome, the frictional force acting against movement emanating from the force exerted by actuator 330 will be constant.

As will be discussed further below, the above mentioned pre-defined trigger release position of trigger element 380, and the corresponding position of needle shield 350, will be situated at the final part of the proximal movement of the needle shield where the snap arms 382 travel along the constant height ramp segments of ramp sections 212.

The high initial needle shield displacement force over a short distance assures that the needle shield is fully displaced and the autoinjector is effectively triggered due to the inertia of the human motion. In accordance herewith, the trigger release position may be positioned at a location where the snap arms 382 slide along the ramp sections 212 at the constant height ramp segments, preferably within the most proximal half of the path of interaction between the snap arms 382 and the constant height ramp segments of ramp sections 212.

The autoinjector may be so configured that the front cover 512 is only penetrated by the front needle 510 once the high initial force for bending the snap arms 382 radially inwards has been overcome, i.e. subsequent to the needle shield having reached the triggering position. Hence, the risk that a non-triggered but broached device may occur will be minimal.

In the following, while mainly referring to FIGS. 1a through 5c, operation of the injection device 100 will be described.

As a first step in operating device 100, the previously mentioned protective cap is removed from the device. As mentioned above, FIGS. 1a-1c show the device in its initial storage condition but with the protective cap being removed from the housing 200/220. The needle shield 350 is in its extended position whereby the front needle 510 is in a shielded state. Also the rear needle 520 is in a shielded state as the cartridge 600 assumes its initial position situated apart from the needle assembly 500.

In accordance with the above description, the housing 200/220 acts as an activator relative to the needle shield 350, in that, as the housing is gripped by the hand of the user and the distal end of device 100 is pressed against an injection site, the needle shield 350 will remain arrested relative to the skin and the housing moves distally relative to the needle shield 350 for activating the expelling assembly of the device 100.

As the device 100 is activated (cf. FIGS. 2a-2c) the needle shield 350 is moved in a proximal direction relative to lower housing section 220 with the distal end surface of the needle shield 350 moving towards the needle assembly 500. The movement brings the front needle 510 through the small aperture 354 in the needle shield 350. As the needle cannula moves relative to the aperture 354 the above mentioned front cover 512 (see FIG. 2c) is preferably held back by the geometry around the aperture 354, thereby allowing the front needle 510 to penetrate the front cover 512 while front cover is being compressed between the needle shield 350 and the needle hub 501. Alternatively the front cover could move through the aperture 354 as well. In such case the front cover would be pressed against the patient's skin, thereby being compressed between the device 100 and the injection site. The compression of the front cover can be either in a concertina-like way or be bent sideways, e.g. radially outwards. The front cover may have a specific geometry to ensure that the front cover is always compressed between needle shield 350 and needle hub 501. The aperture 354 in the needle shield 350 could also have a specific geometry for ensuring correct compression of the front cover.

In the state shown in FIGS. 1a-1c the trigger element 380 is in its distal position due to the pressure exerted by the needle shield spring 340. Cf. to FIG. 9b, the releasable lock that rotationally locks the plunger release element 320 relative to the housing 200/220 is enabled and the drive ram 310 is therefore in its initial position. The cartridge 600 is positioned in its proximal storage position. The snap arms 382 have climbed the ramp sections 212, resulting in the snap arms 382 have been deformed radially inwards by the ramp sections 212 (see FIG. 2c).

As the needle shield 350 reaches a predetermined position, i.e. the proximal collapsed position, the needle shield 350 will reach a stop limit, see FIGS. 2a, 2b and 2c. In this state the front needle 510 is inserted in the patient's skin at full depth and the front cover 512 is compressed (see FIG. 2c). In accordance with the movement of the needle shield 350, the trigger element 380 has been moved into its proximal position, i.e. past the triggering position and even past the trigger release position.

As the trigger element 380 has been moved into its proximal position, the axial tracks 388 of trigger element 380 have become displaced so as to disengage from the engagement with the protrusions 328 of plunger release element 320. This situation is best viewed in FIG. 2a. Due to the actuating spring 330 is exerting a force in the distal direction on drive ram 310 and plunger release element 320 the non-self-locking threaded engagement 325/205 will induce the plunger release element 320 to rotate. In FIGS. 2a and 2b, the plunger release element 320 has been rotated slightly relative to top housing section 200 and, in accordance with the threaded engagement, the plunger release element 320 and the drive ram 310 have been moved slightly axially in the distal direction. The initial spacing between the drive ram 310 and the spacing member 400 has been eliminated so that the force of the actuating spring 330 is enabled to act on the piston 630 of cartridge 600 by means of the drive ram 310 and the spacing member 400.

The needle shield 350 and thus the blocking geometry 351 have been moved in the proximal position so that the resilient arms 530 are free to become deflected outwards. As shown in FIG. 3a-3c—the force from the actuation spring 330 firstly displaces the drive ram 310, the spacing member 400 and the piston 630 a distance in the distal direction. During the first part of this stage the rear needle 520 is still separated from the septum 620 of the cartridge 600 and the cartridge is thus forced to move with the piston 630. The force of actuating spring 330 is sufficient to overcome the force needed for deflecting the resilient arms 530 outwards. Note however, that in FIGS. 3b and 4b, the resilient arms 351 are shown superposed relative to the wall sections of the cartridge 600. A more correct depiction of how the resilient arms 351 are actually deflected can be viewed in FIGS. 3c and 4b.

Initially, as the cartridge 600 moves distally, the distance between the stop surface 401 of the spacer element 400 and the rear end 611 of the cartridge 600 remains unchanged as the piston 630 generally does not move relative to the body of the cartridge 600. However, after the cartridge 600 has been moved fully in the distal direction, the piston 630 begins its movement inside cartridge 600, the said distance decreases.

In the state shown in FIG. 3c cartridge 600 has been moved fully into its distal active position where it meets a stop feature formed in the needle hub 501. The rear needle 520 has penetrated the rear cover 522 and the rear cover has been compressed by the force exerted by the septum 620 of cartridge 600. Further, the rear needle 520 has penetrated the septum 620 of the cartridge. Hence, fluid communication between the needle cannula and the medicament contained in the cartridge 600 has been enabled. In this position the needle cannula is in contact with both the patient's skin and the medicament contained in the cartridge 600. After fluid communication between needle cannula and cartridge 600 is established the medicament is injected into the patient by means of the drive ram 310 being now forced relative to top housing section 200 and being urged distally by actuating spring 330. In the state shown in FIGS. 3a and 3b, the force exerted by the actuating spring 330 has acted on the drive ram 310 for expelling a first portion of the fluid from the cartridge 600.

The actuating spring 330 continues to act on the piston 630 advancing the piston to a predefined end of dose position determined by the end of dose feature. When the stop surface 401 of spacer element 400 reaches the rear end 611 of the cartridge 600 the movement of the drive ram 310 is stopped, thereby stopping the expelling of the medicament (cf. FIG. 4b).

FIGS. 5a-5c shows the injection the device 100 after it has been retracted relative to the injection site. As the device is removed the needle shield 350 is moved forward relative to the lower housing section 220, the needle shield being urged by means of the needle shield spring 340, thereby releasing the compressive pressure on the front cover (not shown). In the shown embodiment, the front cover 512 remains in its collapsed position. In alternative embodiments the front cover will tend to return to its extended position covering the front needle 510.

As the device 100 is moved away from the patient the front needle 510 is removed from the skin of the patient. In embodiments where said front cover returns to its extended position, the front cover will prevent any excess medicament that is expelled from the needle cannula from dripping out of the device. The rear cover remains in its collapsed position due to the pressure from the cartridge 600.

As discussed above the needle shield 350 includes a lock which renders the needle shield 350 locked against proximal movements once it has been returned from the proximal collapsed position to the distal extended position, i.e. where the front needle 510 is in its shielded state. Referring particularly to FIG. 5c, in the final state of the autoinjector, the resilient arms 392 have been pressed radially outwards into their biased active configuration by resilient parts 403 of the thrust arms 402 of spacing member 400. As the protrusions of the resilient arms 392 have been axially aligned with the corresponding recesses 202 in housing 200, the radially outwards movement of resilient arms 392 are allowed and hence the resilient arms 392 are moved into locking engagement directly with the housing section 200.

Close inspection of FIG. 5c reveals that a proximal surface of each of the protrusions and the corresponding distal surface of the recesses 202 are formed with inclined sections tending to move the resilient arms outwards when increasing pressure is exerted in the proximal direction on needle shield 350. Hence, the locking of the needle shield in the distal extended position is effectively obtained even when excessive forces are applied onto the needle shield 350. In this state the autoinjector is ready for disposal.

FIGS. 10a-10d are cross sectional side views of an exemplary embodiment of an autoinjector 100' in accordance with the invention, each view depicting one of four different operational states during the triggering procedure of the device. Generally, the shown autoinjector 100' is functionally similar to the embodiment 100 shown in FIGS. 1a through 9c.

However, features that relate to the trigger operation have been modified relative to the autoinjector 100. Whereas the autoinjector 100 shown in FIGS. 1a through 9c includes a mechanism providing interaction between snap arms 382 and ramp sections 212 for generating a resistance to movement of the needle shield during needle shield displacement from the initial extended position towards the collapsed position, the autoinjector 100' includes a modified design omitting the said snap arms 382 and ramp sections 212.

FIG. 10a shows the autoinjector 100' in a state where a removable protective cap 230 is attached to a distal end of the device 100' to protect the needle end of the device. In FIG. 10a the autoinjector 100' is in its initial storage state where the needle shield 350 is in its initial distal extended position wherein the needle assembly 500 is arranged separated from a proximal surface of the needle shield 350 and separated from a distal end surface of the cartridge 600. The needle assembly 500 includes a penetrable front needle cover 512 and a penetrable rear needle cover 522 respectively forming sterility sheaths for the front needle 510 and rear needle 520.

Again, the autoinjector 100' includes a plunger arrangement comprising a drive ram 310 and spacer member 400. A rotatable plunger release element 320' functions as a plunger release controller for controlling release of the plunger arrangement. The drive ram 310 accommodates an actuating spring 330 and transfers the released actuating force through a spacer member 400 towards the piston of the cartridge 600. In the shown embodiment the spacer member 400 is mounted axially slideable but prevented from rotating relative to the housing. In the shown embodiment the drive ram 310 is not constrained rotationally in the housing. The plunger release element 320' is freely rotatable relative to drive ram 310. Hence, the plunger release element easily rotates relative to the housing independent from rotational characteristics of the drive ram.

For the autoinjector 100', FIGS. 11a through 11d provide representation of a modified trigger element 380', a modified top housing section 200' and a modified plunger release element 320'.

FIG. 11a shows a perspective view of the modified trigger element 380' offering a view of one of a plurality of axial tracks 386' that are formed at an exterior surface of the trigger element 380' and arranged at the proximal end thereof. FIG. 11b shows a perspective partly cut view of the trigger element 380' and a proximal fragment of top housing section 200'. Top housing section 200' includes a plurality of axial ribs 206' arranged at an inner surface to cooperate with respective axial tracks 386' of trigger element 380'. This arrangement prevents the trigger element 380' from rotating relative to the housing 200'/220 but enables axial displacement of the trigger element 380'. Axial stops are further formed for limiting the axial movement of trigger element 380' and needle shield 350 relative to housing 2007220 between the initial extended position to the proximal end position, i.e. the collapsed position. As noted above, the needle shield and the trigger element are movable through the intermediately located triggering position and trigger release position.

FIG. 11c is a partly cut perspective view of the modified trigger element 380'. Arranged at the proximal end of the trigger element 380', on a radially inward facing wall thereof, a plurality of control tracks 388' are formed where each control track 388' is configured to cooperate with a respective track follower 328' provided as a protrusion on a radially outwards facing surface of plunger release element 320' (see FIG. 11d). In the embodiment shown on FIG. 11c, the control track 388' comprises three consecutive segments, i.e. a first control track segments 388'a, a second control track segment 388'b and a release segment 388'c. The first control track segment 388'a includes an angled surface that is inclined with respect to the first rotational axis. Also, the second control track segment 388'b includes an angled surface that is inclined with respect to the first rotational axis but having a different orientation than the first control track segment 388'a. The proximal end of the second control track segment 388'b connects to the distal end of the first control track segment 388'a whereas the distal end of the first control track segment 388'b connects to the release segment 388'c.

In the shown embodiment, the track follower 328' of the modified plunger release element 320' exhibits a surface 328'a that is inclined with respect to the first rotational axis and in a way which corresponds to the inclined surface of the first control track segment 388'a so that when the autoinjector 100' assumes its initial state, i.e. the storage state, the surface 328'a is in intimate contact with at least a portion of the angled surface of the first control track segment 388'a.

FIGS. 12a-12c show schematic representations of the trigger element 380' and the plunger release element 320' in different states throughout the triggering procedure. For illustrative purposes, the remaining components have been omitted from FIGS. 12a-12c and a side portion of the trigger element 380' has been cut away offering a view of the distal portion of the plunger release element 320'.

FIG. 12a shows the trigger element 380' and the plunger release element 320' in the initial state, cf. to FIG. 10a. In this state the surface 328'a of plunger release element 320' is located at the first control track segment 388'a of the trigger element 380'. Due to the force exerted by the actuating spring 330 on the drive ram and the threaded connection 325'/205' between the plunger release element 320' and the top housing section 200', a torque is exerted on plunger release element 320' for rotating the plunger release element 320' relative to the trigger element 380' in the expelling rotational direction so that the surface 328'a and the first control track segment 388'a are in abutment. The expelling rotational direction of the shown embodiment is the clockwise direction when viewed in the distal direction.

FIG. 10b shows the autoinjector 100' in a state where the cap 230 has been removed and the autoinjector 100' has been initially applied to an injection site applying a deliberate force on the housing of the device for triggering the device. The needle shield 350 and the trigger element 380' have been slightly forced in the proximal direction against the force of needle shield spring 340. Referring to FIG. 12b which shows the trigger element 380' and the plunger release element 320 in positions corresponding to the state shown in FIG. 10b, due to the inclination of the surface 328'a and the first control track segment 388'a, the plunger release element 320' has been induced to rotate in the rotational direction opposite the expelling rotational direction in the course of the first control track segment 388'a of the trigger element 380' having been moved proximally along the surface 328'a of plunger release element 320'. Correspondingly, the plunger release element 320' is rotated in accordance with the threaded connection 205'/325' relative to the housing against the force of the actuating spring 330. In other words, the protrusion 328' travels uphill as the protrusion 328' slides up the inclined surface of the first control track segment 388'a.

As the actuating spring 330 exerts a considerable torque on the plunger release element 320' (by means of threaded connection 205'/325') the resistance against moving the needle shield 350 in the proximal direction is relatively high, the resistance being largely decided by straining of the shield spring, the friction for moving the needle shield and the trigger element axially and the straining of the actuating spring. In the state shown in FIGS. 10b and 12b, the tip of the front needle 510 is still situated spaced away from the proximal surface of the needle shield 350 so that the front cover 512 has not yet been penetrated by the front needle 510 and the front cover has not yet been broached.

Theoretically, should the user wish to abort the triggering procedure at this point, the needle shield would be forced to return to the initial extended position, driven by the force of the needle shield spring 340 and the torque emanating from the actuating spring 330. Consequently, the plunger release element 320' would rotate back as the trigger element 380' would travel back to the location shown in FIGS. 10a and 12a. It is to be noted that in the state shown in FIGS. 10b and 12b the autoinjector 100' is not triggered for expelling a dose of drug as the plunger release element 320' is not yet able to rotate freely. However, in practice, the high initial needle shield displacement force over a short distance assures that the needle shield is fully displaced and the autoinjector is effectively triggered due to the inertia of the human motion. The state shown in FIGS. 10b and 12b the components effectively defines the above described triggering position.

In the shown example, the axial displacement of the needle shield from the state shown in FIG. 10a to the state shown in FIG. 10b may be selected within the range of fractions of millimetres to a few millimetres, such as within 1, 2 or 3 millimetres.

In the shown embodiment, when the needle shield 350 has been moved further proximally than shown in FIG. 12b, the inclined surface of the second control track segment 388'b will be forced to slide over the protrusion 328' of plunger release element 320'. When the protrusion 328' is situated along segment 388'b the protrusion may be considered to travel downhill. This downhill movement is aided by the torque emanating from actuating spring 330 and acting on plunger release element 320' in the expelling rotational direction. As a consequence, the inertia of the human motion is allowed to progress unhindered only counteracted by the needle shield spring 340 and the autoinjector 100' is moved further relative to the injection site meaning that the needle shield 350 will be moved fully towards the collapsed position.

FIG. 10c and FIG. 12c show the autoinjector 100' in a state where the needle shield 350 enters into a trigger release position where the plunger release element 320' will be fully released from cooperation with the trigger element 380'. This is accomplished by the trigger element 380' having been moved so that the protrusion 328' of plunger release element 320' meets the release segment 388'c. In the shown example, when the needle shield 350 assumes its trigger release position, the tip of the front needle 510 has penetrated the front cover 512 and the tip of the front needle protrudes distally from the needle shield 350. Release segment 388'c exhibits a steeply inclined surface so that the plunger release element 320' will be allowed to rotate unhindered.

FIG. 10d shows this situation with the autoinjector 100' in a state where the needle shield 350 has entered into the collapsed position and the trigger element 380' has been moved fully proximal. Hence, the front needle 510 extends fully from the autoinjector corresponding to the pre-defined needle insertion depth. In FIG. 10d the plunger release element 320' has been allowed to rotate relative to the trigger element 380' to an extent so that the thread 325' has been moved approximately halfway out of the thread 205'. The plunger release element 320' and the drive ram 310 have consequently moved slightly in the distal direction forced by the axial force exerted by the actuating spring 330.

Distally to the release segment 388'c the trigger element 380' forms an opening having no parts that would interfere with the rotational and axial movement of the plunger release element 320'. Hence, once the protrusion 328' enters said opening, the plunger release element 320' rotates in accordance with the threaded connection 205'/325' until the thread 325' of the plunger release element escapes the thread 205' of the top housing section 200'. In the shown embodiment, the threaded engagement is maintained while the drive ram 310 moves the cartridge distally in a first partial displacement.

In the shown embodiment the threaded connection is maintained for approximately one complete revolution of the plunger release element 320'. The threaded engagement is maintained during about 80% of the total cartridge displacement and serves to reduce the speed of the drive ram as it moves distally prior to the expelling stage. In the shown embodiment, by utilizing the length of the threaded connection, the speed of the drive ram 310 will be reach approximately half the velocity compared to the velocity of a corresponding drive ram not being controlled by the plunger release element 320', i.e. wherein a drive ram would be instantaneously released and pressed forward in a purely axial translational movement for the same axial displacement. Said reduction in speed is beneficial to reduce impacts prior to the expelling procedure.

After the thread 325' of the plunger release element 320' escapes the thread 205' of the top housing section 200' the drive ram 310 will continue to move axially in the distal direction, initially for moving the cartridge 600 fully into its active position, and subsequently for expelling the dose of drug from the cartridge. The further operation of the autoinjector 100' will not be described herein as this generally corresponds to the operation principle described above in connection with the embodiment of the autoinjector 100 shown in FIG. 1*a* through 9*c*.

It is to be noted that although the above described trigger element 380' shows control tracks 388' made up of rectilinear control track segments, the slope of the inclined surfaces of each said segments may be made non-linear such as by forming curved stretches for controlling the resistance against moving the needle shield 350 relative to the housing 200'/220 as a function of distance travelled. Further, the slope of inclination of the individual segments may be made continuous or discontinuous. Also, the number of segments making up the control track 388 may be made different than the shown three-segment control track.

FIG. 13*a* shows a trigger element 380" in accordance with a further embodiment of the invention, wherein the control tracks 388" have been modified relative to the control track of trigger element 380' shown in FIG. 11*c* in that each of the control tracks 388" only defines two consecutive segments, i.e. a first control track segment 388"*a* and a release segment 388"*c*. The first control track segment 388"*a* includes an angled surface that is inclined with respect to the first rotational axis so that the user needs to exert a force for overcoming the torque exerted on plunger release element 320' and emanating from the actuator 330.

Due to the inclination of the surface 328'*a* and the first control track segment 388'*a*, the plunger release element 320' will be induced to rotate in the rotational direction opposite the expelling rotational direction in the course of the first control track segment 388"*a* of trigger element 380" having been moved proximally along the surface 328'*a* of plunger release element 320'. Correspondingly, the plunger release element 320' is rotated in accordance with the threaded connection 205'/325' relative to the housing against the force of the actuating spring 330. In other words, the protrusion 328' travels uphill as the protrusion 328' slides up the inclined surface of the first control track segment 388"*a*.

In an autoinjector 100' that includes the modified trigger element 380", the penetration of the front cover 512 by the front needle 510 may be performed when the needle shield 350 has moved the trigger element 380" proximally so that the protrusions 328' of plunger release element 320' are situated at the distal end of the control track segment 388"*a*, i.e. shortly before the trigger element 380" has passed the trigger release position.

FIG. 13*b* shows a trigger element 380''' in accordance with a still further embodiment of the invention, wherein the control tracks 388''' have been modified relative to the control track 388" of trigger element 380" shown in FIG. 13*a*. In FIG. 13*b*, the first control track segment 388''' includes an inclined surface with a different inclination, e.g. having a slope oppositely disposed than the inclined surface of the first control track segment 388"*a* of trigger element 380". When the protrusion 328' is situated along control track segment 388'''*a* the protrusion 328' of the plunger release element 320' may be considered to travel downhill. Apart from the force exerted by needle shield spring 340, an initial reluctance of moving the needle shield 350 relative to the housing 200'/220 for triggering the device mostly originates from static friction between components that move during the triggering procedure. By forming the first control track segment 388'''*a* in the way shown in FIG. 13*b*, the said inclination may act to reduce frictional forces between the control track segment 388''' and the protrusion 328' and may even act to assist moving the trigger element 380''' in the proximal direction. By appropriately designing the inclined surface, the force constant of the shield spring, the force constant of the actuator spring and the threaded connection 325'/205' the triggering mechanism may be optimised for a particular desired performance.

For the above described embodiments, such as the ones shown in FIGS. 11*c* and 11*d* and the embodiments shown in FIGS. 13*a* and 13*b*, it is to be noted that the protrusion 328' of the plunger release element 320' needs not exhibit a surface 328'*a* that is inclined, such as in the way shown in FIG. 11*d*.

The above described snap mechanism described in connection with the embodiment shown in FIGS. 1*a* through 9*c* where snap arms 382 of the trigger element 380 engage the ramp sections 212 of the housing 200/220 may in further embodiments be combined with the principles of the control tracks and the cooperating track followers as discussed in relation to FIGS. 10*a* through 13*b*.

In further alternative embodiments which are not shown in the figures, in accordance with the principles set forth above, the control track of the trigger element may be alternatively disposed on the plunger release element to cooperate with a track follower arrangement disposed on the trigger element. Such configuration would still provide the same possibility of controlling the force needed to move the needle shield 350 relative to the housing 2001/220 for triggering the device by partly using the torque that acts on the plunger release element and that emanates from the actuating spring 330.

As described above, the control track is used for inducing rotation of the plunger release element as the needle shield is moved from the initial extended position to the trigger release position. In further alternative embodiments which are not shown in the figures, but still in accordance with the principles set forth above, instead of forming the control track and the track followers on the trigger element and the plunger release element, the disclosed arrangement of the control track and the track follower may alternatively be arranged on the trigger element and the housing. As an example, such design may be accomplished with a trigger element defining axial tracks 386 that extend parallel with the first rotational axis and which cooperate with protrusions 328 on the plunger release element 320. In such a device, the plunger release element 320 will not rotate relative to the trigger element as long as the trigger element prior to triggering is moved between the initial extended position and the triggering position. However, if the trigger element comprises control tracks having one or more segments having inclined surfaces and the housing defines track followers that cooperate with such inclined surfaces, the trigger element will be induced to rotate slightly as the needle shield is moved from the initial extended position to the triggering position. Consequently, the plunger release element is also forced to rotate slightly in the expelling rotational direction or against the expelling rotational direction depending on the slope of the inclined surface of the control track. Alternatively, the same effect can be accomplished if the inclined surface segments of the control track are defined by the housing to cooperate with track followers defined by the trigger element.

In accordance with a first type of autoinjector described above, a trigger principle has been described wherein a plunger is operatively coupled to a threaded component that is in engagement with a base thread. The plunger is maintained in pre-triggering state by means of the threaded connection wherein relative rotation between the threaded component and the base thread is prevented. Upon being triggered, the threaded component and the base thread are allowed to rotate relative to each other ultimately allowing the plunger arrangement to move in a distal direction.

In accordance with the general principle, in a second type of autoinjector, the above described trigger principle may be used in an alternative autoinjector which is slightly modified relative to the first type autoinjector. The modifications mainly rely in that the plunger release element associated with the plunger may be prevented from being rotated both during storage and during operation of the autoinjector. Instead the base thread may be arranged on a rotatable component which during storage is prevented from rotating relative to the housing. The rotatable component of the injector is rotatably mounted relative to the housing but may be prevented from moving axially relative to the housing. Subsequent to triggering, the rotatable component is allowed to rotate relative to the plunger release element in accordance with the threaded connection between the base thread component and the thread of the plunger release element. Optionally, for providing a similar effect as described in connection with FIGS. 10*a* through 13*b*, during needle shield displacement from the initial extended position towards the triggering position, the rotatable component is slightly rotated by operating the base thread component relative to the thread of the plunger release element.

Reference is made to FIG. 14, which shows the basic components needed for such a second type autoinjector. Comparing FIG. 9*b* and FIG. 14, the above described embodiments are modified in defining a rotatable component 1204 which is rotatably mounted relative to the housing 1200 but prevented from moving axially. The rotatable component 1204 defines a base thread component 1204 defining a thread 1205. The plunger release element 1320 defines a thread 1325 adapted to initially engage the thread 1205 of the rotatable component 1204. The plunger release element 1320 is prevented from rotating relative to the housing. The means for preventing said rotation may for example be provided by forming an axial track 1321 of the plunger release element 1320 that engages a not shown geometry of the drive ram. The drive ram may be made non-rotatable by forming appropriate rotational locks between the drive ram, the spacing member and the housing. In other embodiments, as neither the plunger release element 1320, the drive ram and the spacer member are configured for rotation, the plunger arrangement may be formed by components that are fixedly attached relative to each other or made as a unitary component.

In the embodiment shown in FIG. 14, the trigger element 1380 is prevented from rotating relative to the housing 1200. The trigger element 1380 is modified by having rotation controlling geometries 1388 that cooperate with corresponding protrusions 1208 of the rotatable component 1204. The rotatable component 1204 is biased in an expelling rotational direction by being urged by the actuating spring. When the trigger element 1380 assumes its initial extended position, the rotation controlling geometries 1388 cooperate with the protrusions 1208 of the rotatable component 1204 to thereby prevent the rotatable component from rotating in the expelling rotational direction. When the autoinjector is to be triggered, the trigger element 1380 is pushed proximally towards its triggering position. This displaces the rotation controlling geometries 1388 relative to the protrusions 1208. Due to threaded engagement between threads 1325/1205, the force emanating from the actuating spring will tend to rotate the rotatable component 1204. Once the trigger element 1380 has been moved proximally relative to the trigger release position, the rotatable component 1204 is now allowed to rotate freely due to the rotation controlling geometries 1388 have become disengaged relative to the protrusions 1208.

The above described effect of controlling the force reaction on the needle shield by using the force of the actuating spring may be utilized by appropriately forming the rotation controlling geometries 1388 and the protrusions 1208 so that the rotatable component 1204 may be forced to slightly rotate as the trigger element 1380 is moved proximally from the initial extended position and towards the triggering position. It is to be noted that a corresponding effect may be obtained if the rotation controlling geometries are instead formed on the rotatable component to cooperate with protrusions disposed on the trigger element.

Still in accordance with the general principle, instead of having the trigger element being rotatably fixedly mounted relative to the housing, the trigger element may be made rotationally fixed but axially movable relative to one of the plunger and the rotatable component and configured to induce relative rotation of the other one of the plunger and the rotatable component as the trigger element moves from the initial extended position towards the triggering position.

Some preferred embodiments have been shown in the foregoing, but it should be stressed that the invention is not limited to these, but may be embodied in other ways within the subject matter defined in the following claims.

The invention claimed is:
1. An autoinjector for being triggered for expelling a single dose of a drug from a drug cartridge, when present, the autoinjector comprising:
   a base,
   the drug cartridge arranged relative to the base, the drug cartridge comprising:
   a) an elongated body having a distal end and a proximal end and defining a central longitudinal axis, the body having a distally arranged outlet adapted for connection to a held needle, and b) a piston accommodated in the body, the piston configured for being driven axially in a distal direction to expel the dose of the drug through the outlet, a plunger adapted upon triggering for moving in the distal direction relative to an initial axial position and transferring a force to move the piston, an actuator providing stored energy, the actuator configured for providing a force to act on the plunger to drive the piston distally, a needle shield axially movable relative to the base in a proximal direction from an initial extended position via a triggering position to a trigger release position, wherein a plunger release element is operatively coupled to the plunger to prevent the plunger from moving distally relative to the plunger release element, wherein the plunger release element defines a thread and the base associates with a base thread component that defines a thread adapted for engaging with the thread of the plunger release element, wherein the needle shield is operatively coupled to the plunger release element and the base thread component to define a releasable retaining mechanism configured to, in an initial state where the needle shield assumes the initial extended position, retain the plunger release element threadedly engaged with the base thread component in a predefined relative rotational and axial position where the force of the actuator provides bias for urging relative rotation between the plunger release element and the base thread component in an expelling rotational direction, wherein the needle shield is configured for operating the retaining mechanism to release the retaining of the plunger release element and the base thread component from the predefined relative rotational and axial position upon the needle shield being moved into the trigger release position, and wherein a first pair of cooperating structures operatively couples the needle shield with the base and a second pair of cooperating structures operatively couples the needle shield with the plunger release element, the first pair of cooperating structures and the second pair of cooperating structures being configured to induce relative rotation between the plunger release element and the base thread component as the needle shield moves from the initial extended position towards the triggering position wherein the energy stored in the actuator is configured to change as the needle shield moves from the initial extended position towards the triggering position.

2. The autoinjector as defined in claim 1, wherein the thread of the plunger release element is rotatable relative to the base and the base thread component is non-rotatable relative to the base.

3. The autoinjector as defined in claim 2, wherein the second pair of cooperating structures defines a first control track comprising an inclined surface which forms an angle relative to a first rotational axis, the first control track being defined by one of the needle shield and the plunger release element, and wherein the other of the needle shield and the plunger release element defines a first track follower configured for engaging said first control track.

4. The autoinjector as defined in claim 3, wherein the first pair of cooperating structures defines an axial track formed by one of the needle shield and the base and wherein the other of the needle shield and the base defines a second track follower configured for engaging said axial track.

5. The autoinjector as defined in claim 3, wherein the first control track and/or a second control track defines consecutive first and second control segments, wherein the first control segment comprises a surface having a first degree of inclination and the second control segment comprises a surface having a second degree of inclination different from the first degree of inclination.

6. The autoinjector as defined in claim 2, wherein the first pair of cooperating structures defines a first control track comprising an inclined surface which forms an angle relative to a first rotational axis, the first control track being defined by one of the needle shield and the base, and wherein the other of the needle shield and the base defines a first track follower configured for engaging said first control track.

7. The autoinjector as defined in claim 6, wherein the second pair of cooperating structures defines an axial track formed by one of the needle shield and the plunger release element, and wherein the other of the needle shield and the plunger release element defines a second track follower configured for engaging said axial track.

8. The autoinjector as defined in claim 6, wherein the second pair of cooperating structures defines a second control track comprising an inclined surface which forms an angle relative to the first rotational axis, the second control track being defined by one of the needle shield and the plunger release element, and wherein the other of the needle shield and the plunger release element defines a second track follower configured for engaging said second control track.

9. The autoinjector as defined in claim 1, wherein the releasable retaining mechanism defines a lock, wherein the held needle defines a front needle configured to be manually operable relative to the needle shield such that, when the needle shield is held against an injection site, manual operation of the front needle relative to the needle shield or vice versa causes manual penetration of the front needle into the injection site and causes subsequent release of the lock.

10. The autoinjector as defined in claim 1, wherein at least part of said induced relative rotation between the plunger release element and the base thread component acts to provide relative rotation counter to the expelling rotational direction as the needle shield moves from the initial extended position towards the triggering position to increase the energy stored in the actuator.

11. The autoinjector as defined in claim 10, wherein at least part of said induced relative rotation between the plunger release element and the base thread component acts to provide relative rotation in the expelling rotational direction as the needle shield moves from the triggering position towards the trigger release position to decrease the energy stored in the actuator.

12. The autoinjector as defined in claim 1, wherein at least part of said induced relative rotation between the plunger release element and the base thread component acts to provide relative rotation in the expelling rotational direction as the needle shield moves from the initial extended position towards the triggering position to decrease the energy stored in the actuator.

13. The autoinjector as defined in claim 12, wherein a penetrable needle cover initially covers a distal pointed tip of the held needle, and wherein the distal pointed tip of the held needle is configured for penetrating the penetrable needle cover as the needle shield moves from the triggering position towards the trigger release position.

14. The autoinjector as defined in claim 1, wherein the held needle is mounted relative to the base at a fixed axial position.

15. The autoinjector as defined in claim 1, wherein a needle shield spring acts to bias the needle shield towards the initial extended position.

16. The autoinjector as defined in claim 1, wherein a penetrable needle cover initially covers a distal pointed tip of the held needle, and wherein the distal pointed tip of the held needle is configured for penetrating the penetrable needle cover as the needle shield moves from the triggering position towards the trigger release position.

* * * * *

UNITED STATES PATENT AND TRADEMARK OFFICE
CERTIFICATE OF CORRECTION

| | |
|---|---|
| PATENT NO. | : 11,260,176 B2 |
| APPLICATION NO. | : 16/067214 |
| DATED | : March 1, 2022 |
| INVENTOR(S) | : Soeren Kjellerup Hansen |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this
Tenth Day of June, 2025

Coke Morgan Stewart
*Acting Director of the United States Patent and Trademark Office*